(12) United States Patent  
Hilscher et al.

(10) Patent No.: US 7,770,251 B2
(45) Date of Patent: *Aug. 10, 2010

(54) METHOD AND DEVICE FOR CLEANING TEETH

(75) Inventors: Alexander Hilscher, Kronberg (DE); Horst Mannebach, Münstermaifeld (DE); Hansjörg Reick, Steinbach (DE); Armin Schwarz-Hartmann, Wendelsheim (DE); Peter Trawinski, Weiterstadt (DE); Martin Stratmann, Frankfurt (DE); Wolfgang Vorbeck, Idstein-Eschenhahn (DE)

(73) Assignee: Braun GmbH, Kronberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/872,016

(22) Filed: Jun. 18, 2004

(65) Prior Publication Data

US 2005/0000044 A1 Jan. 6, 2005

Related U.S. Application Data

(63) Continuation of application No. 10/662,237, filed on Sep. 15, 2003, now Pat. No. 7,024,717, which is a continuation of application No. PCT/EP01/02844, filed on Mar. 14, 2001.

(51) Int. Cl.
*A61C 17/22* (2006.01)
*A46B 13/02* (2006.01)

(52) U.S. Cl. .......................................... 15/22.1; 15/28

(58) Field of Classification Search ................... 15/22.1, 15/22.2, 23, 28
See application file for complete search history.

(56) References Cited

U.S. PATENT DOCUMENTS

| 2,798,241 A | 7/1957 | Cohen |
| 3,109,619 A | 11/1963 | Krug et al. |
| 3,220,039 A | 11/1965 | Deyton et al. |
| 3,417,417 A | 12/1968 | Rhodes |
| 3,461,874 A | 8/1969 | Martinez |

(Continued)

FOREIGN PATENT DOCUMENTS

CN 2149877 12/1923

(Continued)

OTHER PUBLICATIONS

Color photographs of Bausch & Lomb "Interplak" Model PB-4B style Handpiece with travel protection switch and Toothbrush attachment (handpiece stamped "1D 1 A", believed circa 1992 on sale in the United States) (2 sheets with 7 views).

(Continued)

*Primary Examiner*—Randall Chin
(74) *Attorney, Agent, or Firm*—John P. Colbert; Vladimir Vitenberg

(57) ABSTRACT

A method and a device for cleaning teeth wherein a variety of cleaning tools are coupled to a common handle section for the individual cleaning of teeth. It relates in particular to a handle section of an electric dental cleaning device, with a coupling section for coupling various cleaning tools thereto, as well as said cleaning tools. According to the invention the handle section detects a coding provided on the respective cleaning tool attached. In dependence upon the respective coding detected, various functions of the dental cleaning device are controlled.

39 Claims, 24 Drawing Sheets

U.S. PATENT DOCUMENTS

| | | |
|---|---|---|
| 3,496,500 A | 2/1970 | Romary |
| 3,571,544 A | 3/1971 | Sheehan |
| 3,782,799 A | 1/1974 | Hansen |
| 3,796,850 A | 3/1974 | Moreland, II et al. |
| 3,810,147 A | 5/1974 | Lichblau |
| 3,802,420 A | 8/1974 | Moffat et al. |
| 3,904,641 A | 9/1975 | Swatman |
| 4,156,620 A | 5/1979 | Clemens |
| 4,274,070 A | 6/1981 | Thiene |
| 4,333,197 A | 6/1982 | Kuris |
| 4,349,814 A | 9/1982 | Akehurst |
| 4,352,098 A | 9/1982 | Stephen et al. |
| 4,365,376 A | 12/1982 | Oda et al. |
| 4,371,118 A | 2/1983 | Sontheimer et al. |
| 4,413,199 A | 11/1983 | Fischer |
| 4,492,574 A | 1/1985 | Warrin et al. |
| 4,502,497 A | 3/1985 | Siahou |
| 4,506,400 A | 3/1985 | Klein |
| 4,514,172 A | 4/1985 | Behringer |
| 4,523,083 A | 6/1985 | Hamilton |
| 4,546,266 A | 10/1985 | Zenick et al. |
| 4,595,850 A | 6/1986 | Woog |
| 4,682,584 A | 7/1987 | Pose |
| 4,698,869 A | 10/1987 | Mierau et al. |
| 4,704,602 A | 11/1987 | Asbrink |
| 4,716,614 A | 1/1988 | Jones et al. |
| 4,736,207 A | 4/1988 | Siikarla et al. |
| 4,820,152 A | 4/1989 | Warrin et al. |
| 4,827,550 A | 5/1989 | Graham et al. |
| 4,845,796 A | 7/1989 | Mosley |
| 4,878,679 A | 11/1989 | Plank et al. |
| 4,900,252 A | 2/1990 | Liefke et al. |
| 4,910,634 A | 3/1990 | Pipkorn |
| 4,914,376 A | 4/1990 | Meyer |
| 5,014,794 A | 5/1991 | Hansson |
| 5,065,137 A | 11/1991 | Herman |
| 5,072,164 A | 12/1991 | Pruis et al. |
| 5,099,536 A | 3/1992 | Hirabayashi |
| 5,165,131 A | 11/1992 | Staar |
| 5,184,959 A | 2/1993 | Oryhon et al. |
| 5,189,751 A | 3/1993 | Giuliani et al. |
| 5,217,478 A | 6/1993 | Rexroth |
| 5,233,323 A | 8/1993 | Burkett et al. |
| 5,263,218 A | 11/1993 | Giuliani et al. |
| 5,269,794 A | 12/1993 | Rexroth |
| 5,289,604 A | 3/1994 | Kressner |
| 5,305,492 A | 4/1994 | Giuliani et al. |
| 5,337,435 A | 8/1994 | Krasner et al. |
| 5,341,534 A | 8/1994 | Serbinski et al. |
| 5,355,544 A | 10/1994 | Dirksing |
| 5,378,153 A | 1/1995 | Giuliani et al. |
| 5,381,576 A | 1/1995 | Hwang |
| 5,392,028 A | 2/1995 | Pichl |
| 5,502,861 A | 4/1996 | Spieler et al. |
| 5,544,382 A | 8/1996 | Giuliani et al. |
| 5,561,881 A | 10/1996 | Klinger et al. |
| 5,576,693 A | 11/1996 | Tyren et al. |
| 5,577,285 A | 11/1996 | Drossler |
| 5,673,451 A | 10/1997 | Moore et al. |
| 5,693,042 A | 12/1997 | Boiarski et al. |
| 5,749,885 A | 5/1998 | Sjostrom et al. |
| 5,760,680 A | 6/1998 | Tyren |
| 5,781,955 A | 7/1998 | Hendricks |
| 5,784,742 A | 7/1998 | Giuliani et al. |
| 5,812,065 A | 9/1998 | Schrott et al. |
| 5,815,872 A | 10/1998 | Meginniss, III et al. |
| 5,864,288 A | 1/1999 | Hogan |
| 5,888,031 A | 3/1999 | Buck et al. |
| 5,897,315 A | 4/1999 | Nakayama et al. |
| 5,939,983 A | 8/1999 | Rudell et al. |
| 5,943,723 A | 8/1999 | Hilfinger et al. |
| 5,974,615 A | 11/1999 | Schwarz-Hartmann |
| 5,998,965 A | 12/1999 | Carlucci et al. |
| 6,017,354 A | 1/2000 | Culp et al. |
| 6,029,303 A | 2/2000 | Dewan |
| 6,043,646 A | 3/2000 | Jansseune |
| 6,140,723 A | 10/2000 | Matsui et al. |
| 6,163,258 A | 12/2000 | Rudell et al. |
| 6,177,870 B1 | 1/2001 | Lian et al. |
| 6,193,510 B1 * | 2/2001 | Tsimerman ................ 433/29 |
| 6,195,828 B1 | 3/2001 | Fritsch |
| 6,202,242 B1 | 3/2001 | Salmon et al. |
| 6,212,052 B1 | 4/2001 | Heuer et al. |
| 6,227,859 B1 | 5/2001 | Sutter |
| 6,234,051 B1 | 5/2001 | Bareggi |
| 6,265,789 B1 | 7/2001 | Honda et al. |
| 6,326,884 B1 | 12/2001 | Wohlrabe |
| 6,353,956 B1 | 3/2002 | Berge |
| 6,359,559 B1 | 3/2002 | Rudell et al. |
| 6,367,108 B1 | 4/2002 | Fritsch et al. |
| 6,389,633 B1 | 5/2002 | Rosen |
| 6,422,566 B1 | 7/2002 | Rudell et al. |
| 6,453,497 B1 | 9/2002 | Chiang et al. |
| 6,531,873 B1 | 3/2003 | Wohlrabe |
| 6,536,068 B1 | 3/2003 | Yang et al. |
| 6,545,576 B1 | 4/2003 | Marchini et al. |
| 6,590,763 B2 | 7/2003 | Kishimoto |
| 6,611,780 B2 | 8/2003 | Lundell et al. |
| 6,623,698 B2 | 9/2003 | Kuo |
| 6,636,135 B1 | 10/2003 | Vetter |
| 6,648,641 B1 | 11/2003 | Viltro et al. |
| 6,731,213 B1 | 5/2004 | Smith |
| 6,734,795 B2 | 5/2004 | Price |
| 6,735,802 B1 | 5/2004 | Lundell et al. |
| 6,750,747 B2 | 6/2004 | Mandell et al. |
| 6,754,928 B1 | 6/2004 | Rosen |
| 6,792,640 B2 | 9/2004 | Lev |
| 6,850,167 B2 | 2/2005 | Rosen |
| 6,868,919 B1 | 3/2005 | Manschitz et al. |
| 6,952,855 B2 | 10/2005 | Lev et al. |
| 6,954,961 B2 | 10/2005 | Ferber et al. |
| 7,024,717 B2 | 4/2006 | Hilscher et al. |
| 7,067,945 B2 | 6/2006 | Grez et al. |
| 7,086,111 B2 | 8/2006 | Hilscher et al. |
| 7,174,972 B2 | 2/2007 | Kristen et al. |
| 7,207,080 B2 | 4/2007 | Hilscher et al. |
| 7,248,892 B2 | 7/2007 | White et al. |
| 7,258,546 B2 | 8/2007 | Beier et al. |
| 7,313,422 B2 | 12/2007 | White et al. |
| 7,373,170 B2 | 5/2008 | White et al. |
| 7,376,439 B2 | 5/2008 | White et al. |
| 2002/0088068 A1 * | 7/2002 | Levy et al. ................ 15/22.1 |
| 2002/0129454 A1 | 9/2002 | Hilscher et al. |
| 2002/0133308 A1 | 9/2002 | Lundell et al. |
| 2002/0196113 A1 | 12/2002 | Rudd et al. |
| 2003/0017874 A1 | 1/2003 | Jianfei et al. |
| 2003/0085687 A1 * | 5/2003 | Stratmann et al. ............ 320/114 |
| 2003/0093103 A1 | 5/2003 | Malackowski et al. |
| 2003/0101526 A1 | 6/2003 | Hilscher et al. |
| 2003/0101528 A1 | 6/2003 | Smith |
| 2003/0115694 A1 | 6/2003 | Pace |
| 2003/0131427 A1 | 7/2003 | Hilscher et al. |
| 2003/0165794 A1 | 9/2003 | Matoba |
| 2004/0220602 A1 | 11/2004 | Deng et al. |
| 2004/0255409 A1 | 12/2004 | Hilscher et al. |
| 2004/0267297 A1 | 12/2004 | Malackowski |
| 2005/0000044 A1 | 1/2005 | Hilscher et al. |
| 2005/0011025 A1 | 1/2005 | Hilscher et al. |
| 2005/0050658 A1 | 3/2005 | Chan et al. |
| 2005/0100867 A1 | 5/2005 | Hilscher et al. |
| 2005/0128051 A1 | 6/2005 | Dickinson et al. |
| 2005/0269403 A1 | 12/2005 | White et al. |
| 2005/0271531 A1 | 12/2005 | Brown, Jr. et al. |
| 2005/0272001 A1 | 12/2005 | Blain et al. |

| | | | | | |
|---|---|---|---|---|---|
| 2005/0272002 A1 | 12/2005 | Chenvainu et al. | EP | 624 079 | 10/1993 |
| 2006/0048797 A1 | 3/2006 | Jung et al. | EP | 634 151 | 1/1995 |
| 2006/0066448 A1 | 3/2006 | Berisford et al. | EP | 787 469 | 8/1997 |
| 2006/0074405 A1 | 4/2006 | Malackowski et al. | EP | 848 921 | 12/1997 |
| 2006/0096046 A1 | 5/2006 | Hilscher et al. | EP | 1267664 | 6/2004 |
| 2006/0145871 A1 | 7/2006 | Donati et al. | EP | 1379149 | 8/2004 |
| 2006/0159533 A1 | 7/2006 | Zeiler et al. | EP | 1244373 | 7/2006 |
| 2007/0001005 A1 | 1/2007 | White et al. | FR | 2832298 | 5/2003 |
| 2007/0234493 A1 | 10/2007 | Hilscher et al. | GB | 1167444 | 10/1969 |
| 2008/0010771 A1 | 1/2008 | Hilscher et al. | GB | 1246564 | 9/1974 |
| 2008/0020351 A1 | 1/2008 | Hilscher et al. | GB | 2082713 | 10/1982 |
| 2008/0020352 A1 | 1/2008 | Hilscher et al. | GB | 2117230 | 10/1983 |
| 2008/0022469 A1 | 1/2008 | Hilscher et al. | GB | 2146893 | 5/1985 |
| 2008/0022470 A1 | 1/2008 | Hilscher et al. | GB | 2376758 | 12/2002 |
| 2008/0022471 A1 | 1/2008 | Hilscher et al. | JP | 1989083268 | 3/1989 |
| 2008/0022501 A1 | 1/2008 | Hilscher et al. | JP | 04-087127 | 3/1992 |
| 2008/0022503 A1 | 1/2008 | Hilscher et al. | JP | 04-269906 | 9/1992 |
| 2008/0028549 A1 | 2/2008 | Hilscher et al. | JP | 05-269024 | 10/1993 |
| 2008/0028587 A1 | 2/2008 | Renault | JP | 08-117030 | 5/1996 |
| 2008/0032265 A1 | 2/2008 | Hilscher et al. | JP | 1996187125 | 7/1996 |
| 2008/0034515 A1 | 2/2008 | Hilscher et al. | JP | 08-275961 | 10/1996 |

FOREIGN PATENT DOCUMENTS

| | | |
|---|---|---|
| JP | 08-000358 | 1/1998 |
| JP | 1998005041 | 1/1998 |
| CN | 2124686 | 12/1992 |
| JP | 1998127346 | 5/1998 |
| CN | 2332378 | 11/1999 |
| JP | 1998137040 | 5/1998 |
| CN | 2048697 | 12/2006 |
| JP | 2862873 | 3/1999 |
| DE | 24 13 524 | 2/1975 |
| JP | 1999113638 | 4/1999 |
| DE | 2826008 A1 | 6/1978 |
| JP | 11-318951 | 11/1999 |
| DE | 28 260 08 C2 | 6/1983 |
| JP | 2001-37788 | 2/2001 |
| DE | 37 08 801 | 9/1988 |
| RU | 749380 | 7/1980 |
| DE | 40 36 973 C2 | 11/1990 |
| RU | 1542539 | 2/1990 |
| DE | 39 37 852 | 5/1991 |
| RU | 1674789 | 9/1991 |
| DE | 3936714 | 5/1991 |
| WO | WO 91/06258 | 5/1991 |
| DE | 4012413 | 10/1991 |
| WO | WO 95/033419 | 12/1995 |
| DE | 40 38 479 | 5/1992 |
| WO | 97/24079 | 10/1997 |
| DE | 42 43 219 A1 | 12/1992 |
| WO | 98/24527 | 6/1998 |
| DE | 3880015 | 9/1993 |
| WO | 98/55274 | 10/1998 |
| DE | 44 22 086 C1 | 6/1994 |
| WO | WO 99/20202 | 4/1999 |
| DE | 40 05 013 | 8/1994 |
| WO | WO 99/053562 | 10/1999 |
| DE | 195 06 129 | 2/1995 |
| WO | 00/74591 | 6/2000 |
| DE | 195 18 935 | 5/1995 |
| WO | 00/39768 | 7/2000 |
| DE | 195 19 935 | 5/1995 |
| WO | 00/42584 | 7/2000 |
| DE | 196 27 752 A1 | 7/1995 |
| WO | 00/47128 | 8/2000 |
| DE | 19506129 | 8/1996 |
| WO | WO 01/32052 | 5/2001 |
| DE | 19628574 | 3/1997 |
| WO | WO 01/47392 | 7/2001 |
| DE | 297 09 865 U1 | 6/1997 |
| WO | 01/08591 | 8/2001 |
| DE | 19545324 | 6/1997 |
| WO | 01/91803 | 12/2001 |
| DE | 29 608 167 | 9/1997 |
| WO | WO 02093881 | 1/2002 |
| DE | 296 08 164 | 4/1998 |
| WO | WO 02/083257 | 10/2002 |
| DE | 299 15 855 U1 | 9/1999 |
| WO | WO 02/098315 | 12/2002 |
| DE | 198 32 607 | 5/2000 |
| WO | WO 03/054771 | 7/2003 |
| DE | 199 21 677 | 11/2000 | | | |
| DE | 199 23 104 A1 | 11/2000 | | | |
| DE | 10001502 | 3/2001 | | | |
| DE | 199 53 651 | 5/2001 | | | |
| DE | 10026513 | 5/2001 | | | |
| DE | 199 53 651 | 10/2001 | | | |
| DE | 10135257 | 2/2002 | | | |
| DE | 10045353 | 3/2002 | | | |
| DE | 10045067 | 4/2002 | | | |
| DE | 10101163 | 7/2002 | | | |
| DE | 10153863 | 5/2003 | | | |
| DE | 10154946 | 5/2003 | | | |
| EP | 024 992 | 6/1984 | | | |
| EP | 046 169 | 8/1984 | | | |
| EP | 0 085 795 | 3/1987 | | | |
| EP | 285 915 | 10/1988 | | | |
| EP | 0300345 | 1/1989 | | | |
| EP | 440 051 | 7/1991 | | | |
| EP | 0435329 | 7/1991 | | | |
| EP | 391 967 B1 | 8/1992 | | | |
| EP | 294 548 B1 | 4/1993 | | | |

OTHER PUBLICATIONS

Package rear and bottom panels of Bausch & Lomb Interplak Model PB-4B, marked © 1990 (color copy, 1 sheet).

Product use instructions to Bausch & Lomb Interplak travel-style "Voyager" model TK-2 marked © 1991 (6 photocopied sheets containing cover and pp. 1-10).

Color photographs of Bausch & Lomb "Interplak" Model PB-6 style Handpiece with waterproof electronic travel protection switch (believed circa 1992 on sale in the United States) (6 views).

Package rear and bottom panels of Bausch & Lomb Interplak Model PB-6, marked © 1992 (color copy, 1 sheet).

"RFID Made Easy" Handbook by EM Microelectronio-Marin SA. 2074 Mann, Switzerland, copr. 2000 and dated Mar. 2001. Rev. C/350, pp. 1-33.

Herzer, Gleshlher, "Der große Lauschangrttf aur Ladendlebe" [transl: "The great surveillance of Shoplifters"] In Phyalkallsche Blätter [transl: Physics Letters] vol. 57 (2001), No. 5, pp. 43-48.

Finkenzeller, Klaus, "RFID-Handbuoh, Grundlagen und praktische Anwendungen induktiver Funkanlagen, Transponder und kontaktloser Chipkarten" [Trans: "RFID Handbook, Fundamentals and practical Applications to inductive radio Communications, Transponders and Contactless Chip Cards"], Carl Hanser Verlag München, 2nd Edition, Chapter 3. pp. 29 to 58 w/ title page and Impreesum, Contents pp. vii-xviii, and Appendices 15.2 "Standards" and 15.3 "Literature" on pp. 393 to 408.
Applicants' U.S. Appl. No. 10/582,237, filed Sep. 15, 2003 publication expected circa Mar. 15, 2005.
PCT Search Report in parent application (U.S. Appl. No. 10/662,237)'s corresponding PCT/EP01/02844, dated Aug. 1, 2001.
PCT Search Report of PCT/EP01/02862 corresponding to co-pending U.S. Appl. No. 09/811,080, dated Jul. 25, 2001.
PCT Search Report of PCT/EP02/01724 corresponding to co-pending U.S. Appl. No. 10/241,274, dated Jul. 10, 2002.
U.S. Appl. No. 11/763,338, filed Jun. 14, 2007.
U.S. Appl. No. 11/888,142, filed Jul. 31, 2007.
U.S. Appl. No. 11/888,249, filed Jul. 31, 2007.
U.S. Appl. No. 11/888,251, filed Jul. 31, 2007.
U.S. Appl. No. 11/888,189, filed Jul. 31, 2007.
U.S. Appl. No. 11/888,211, filed Jul. 31, 2007.
U.S. Appl. No. 11/888,212, filed Jul. 31, 2007.
U.S. Appl. No. 11/888,250, filed Jul. 31, 2007.
U.S. Appl. No. 11/888,152, filed Jul. 31, 2007.
U.S. Appl. No. 11/888,287, filed Jul. 31, 2007.
U.S. Appl. No. 11/888,385, filed Aug. 1, 2007.
U.S. Appl. No. 11/888,386, filed Aug. 1, 2007.
U.S. Appl. No. 11/890,083, filed Aug. 1, 2007.
U.S. Appl. No. 11/257,603, filed Oct. 24, 2005.
Office Action from U.S. Appl. No. 10/872,075 dated Aug. 1, 2006 (15 pages).
Office Action from U.S. Appl. No. 10/872,075 dated Mar. 24, 2006 (19 pages).
Office Action from U.S. Appl. No. 10/872,075 dated Dec. 27, 2006 (11 pages).
Office Action from U.S. Appl. No. 10/872,075 dated May 15, 2007 (9 pages).
Office Action from U.S. Appl. No. 10/872,075 dated Oct. 31, 2007 (8 pages).
Office Action from U.S. Appl. No. 10/872,075 dated Apr. 11, 2008 (4 pages).
Office Action from U.S. Appl. No. 10/871,469 dated Aug. 24, 2005 (19 pages).
Office Action from U.S. Appl. No. 10/871,469 dated Jul. 25, 2006 (11 pages).
Office Action from U.S. Appl. No. 10/871,469 dated Jan. 9, 2007 (3 pages).
Office Action from U.S. Appl. No. 10/871,469 dated Dec. 27, 2007 (7 pages).
Office Action from U.S. Appl. No. 11/763,338 dated Jul. 10, 2008 (20 pages).
Office Action from U.S. Appl. No. 11/763,338 dated Dec. 4, 2008 (20 pages).
Office Action from U.S. Appl. No. 11/257,603 dated Sep. 20, 2006 (6 pages).
Office Action from U.S. Appl. No. 11/257,603 dated Jan. 18, 2007 (7 pages).
Office Action from U.S. Appl. No. 11/257,603 dated May 15, 2007 (6 pages).
Office Action from U.S. Appl. No. 11/257,603 dated Aug. 20, 2007 (12 pages).
Office Action from U.S. Appl. No. 11/257,603 dated Mar. 21, 2008 (21 pages).
Office Action from U.S. Appl. No. 11/257,603 dated Nov. 25, 2008 (16 pages).
Office Action from U.S. Appl. No. 09/811,080 dated Feb. 3, 2004 (19 pages).
Office Action from U.S. Appl. No. 09/811,080 dated Oct. 1, 2004 (8 pages).
Office Action from U.S. Appl. No. 10/241,274 dated Jan. 14, 2005 (4 pages).
Office Action from U.S. Appl. No. 10/241,274 dated Sep. 1, 2006 (14 pages).
Office Action from U.S. Appl. No. 10/662,237 dated Feb. 18, 2005 (6 pages).
Office Action from U.S. Appl. No. 11/888,212 dated Mar. 21, 2006 (6 pages).
Office Action from U.S. Appl. No. 11/888,250 dated Jun. 3, 2008 (6 pages).
Office Action from U.S. Appl. No. 11/888,251 dated Mar. 21, 2008 (7 pages).
Office Action from U.S. Appl. No. 10/872,075 dated Dec. 10, 2008 (15 pages).
Office Action from U.S. Appl. No. 10/872,075 dated Jun. 4, 2009 (19 pages).
Office Action from U.S. Appl. No. 11/763,338 dated Mar. 24, 2009 (20 pages).
Office Action from U.S. Appl. No. 11/888,212 dated Mar. 17, 2009 (11 pages).
Office Action from U.S. Appl. No. 11/888,251 dated Mar. 17, 2009 (22 pages).
Office Action from U.S. Appl. No. 11/888,386 dated Mar. 3, 2009 (24 pages).
Office Action from U.S. Appl. No. 11/890,083 dated Mar. 16, 2009 (35 pages).
Use instructions to Braun D5 electric toothbrush Type 4726 on sale in United States circa 1991 (3 sheets-cover and pp. 8-11) including description of "Travel lock" switch.
Office Action from U.S. Appl. No. 11/890,083 dated Nov. 20, 2009 (7 pages).
Office Action from U.S. Appl. No. 11/888,386 dated Dec. 3, 2009 (10 pages).

* cited by examiner

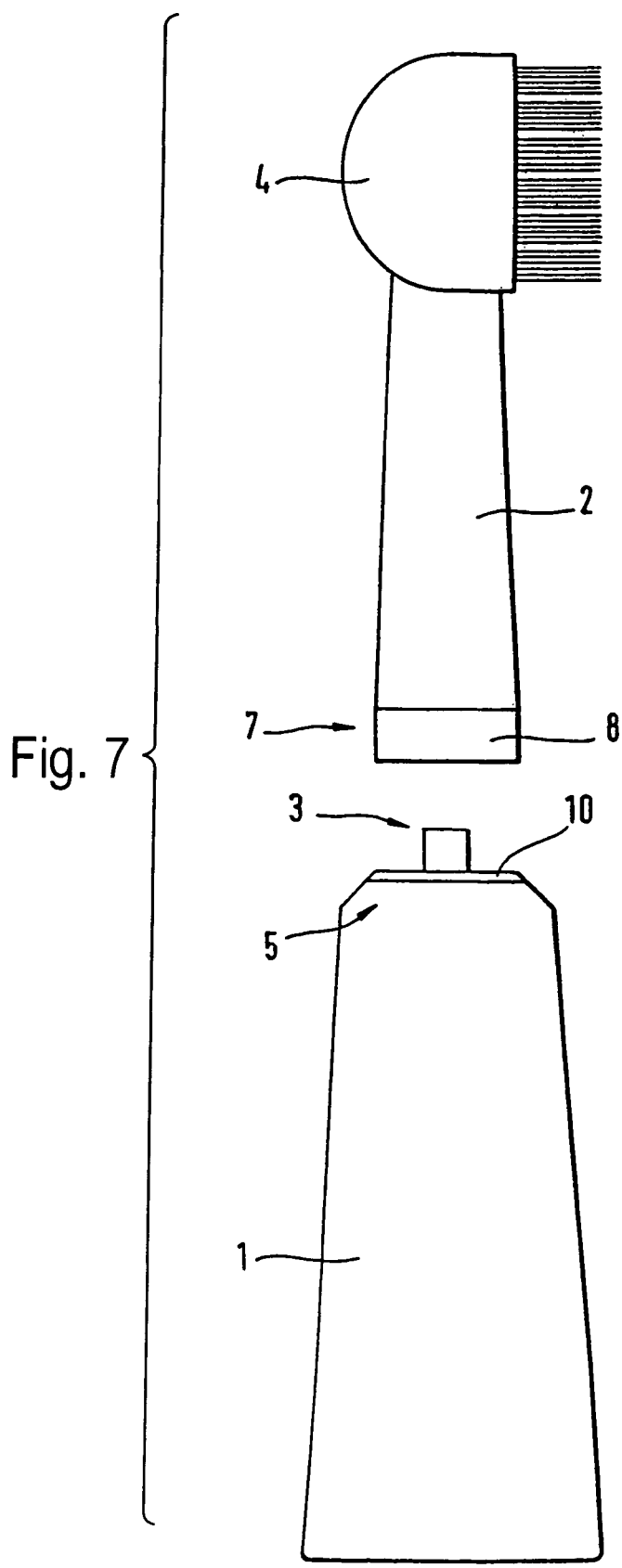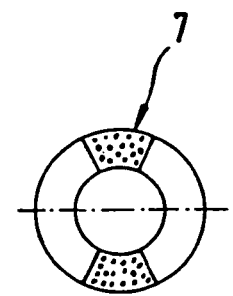
Fig. 7
Fig. 7a

METHOD AND DEVICE FOR CLEANING TEETH

This application is a continuation of U.S. application Ser. No. 10/662,237, filed Sep. 15, 2003, now U.S. Pat. No. 7,024,717, which is a continuation under 35 U.S.C. §120 of PCT International Application No. PCT/EP01/02844, filed Mar. 14, 2001, the contents of which is incorporated reference in its entirety.

This invention relates to a method for cleaning teeth by means of an electric dental cleaning device having coupled to its handle section various cleaning tools for the individual tooth cleaning of the users of the dental cleaning device. The present invention further relates to the handle section of an electric dental cleaning device, in particular toothbrush, which possesses a coupling section for the coupling of a variety of cleaning tools, a drive mechanism for driving the respective coupled cleaning tool, and a control device. The present invention also relates to the cleaning tools, particularly brush attachments, for such a handle section.

Dental cleaning devices such as electric toothbrushes or electric oral irrigators customarily have a grip or a handle section to which a variety of cleaning tools such as brush attachments are attachable, thus enabling several users to use the dental cleaning device with their own, user-related cleaning tools. Such electric toothbrushes are known, for example, from DE 19627752 A1 or EP 0624079 B1. To meet the users' wishes and requirements with regard to the cleaning of their teeth, the respective user has the possibility of individually adjusting dental cleaning parameters such as, for example, the strength of the water jet of oral irrigators or the speed of the brush attachments of electric toothbrushes.

From DE 299 15 858 U1 a dental cleaning device is known in which each of the different toothbrushes can be inserted only into its assigned receptacle in a console. This then starts the program provided for this particular toothbrush. However, children find it particularly difficult to locate the individual opening for insertion of their personal toothbrush and for mating engagement of the plug. Furthermore, this console involves high complexity of manufacture, considering that it requires the provision of a plurality of different receptacles and each of the toothbrushes has a different plug assigned to its own receptacle.

In a further device disclosed in U.S. Pat. No. 5,184,959, each hand toothbrush is assigned its own accommodating slot in a housing, so that each toothbrush can be assigned an individual brushing time signal via the housing. This arrangement is very elaborate from the manufacturing point of view without providing for the detection and storage of user-specific data of the tooth cleaning operation.

Such dental cleaning devices are capable of improvement on many counts. In particular it is desirable to further improve the possible adaptation to the users as well as the user friendliness.

It is an object of the present invention to provide an improved method for cleaning teeth, an improved handle section of an electric dental cleaning device and/or improved cleaning tools that further develop the cleaning of teeth relative to the prior art and afford further advantages. In particular, the invention aims to further improve adaptation to the individual users as well as the user friendliness.

With regard to the method aspects, according to the invention this object is substantially accomplished in a tooth cleaning method of the type initially referred to in that a coding provided on the respective cleaning tool used is detected by the handle section preferably automatically and that, in dependence the detected coding, the handle section controls dental cleaning parameters preferably automatically and/or detects user-specific dental cleaning data preferably automatically.

With regard to the device aspects, according to the invention the object referred to is substantially accomplished in a handle section of an electric dental cleaning device of the type initially referred to in that the handle section possesses a coding detection device to detect an individual coding of the particular cleaning tool attached to the handle section, as well as a control device for the control of at least one function of the dental cleaning device in response to the detected coding. With regard to the cleaning tool of the type initially referred to, the object is accomplished in that it possesses a magnetic, electrical, capacitive, electromagnetic and/or mechanical coding device or a combination of such coding devices.

Accordingly, the handle section detects the cleaning tool just attached and controls, in dependence upon the detected cleaning tool, one or preferably more functions of the dental cleaning device. Assuming, of course, that each handle section user uses his or her own, user-related cleaning tool, the control device of the handle section in particular is capable of establishing automatically, by referring to the coding detected on the cleaning tool, the identity of the user currently using the dental cleaning device. There is no need for any user input as, for example, a fingertip pressure and the like to inform the dental cleaning device of its current user. Hence an automatic adaptation to the respective user can also be made. This results in a maximum of user friendliness.

In particular in a further feature of the invention the control device is capable of adapting operating parameters such as cleaning frequency, cleaning speed and cleaning time or threshold value or desired range of application pressure automatically to the individual user identified. A variety of user profiles can be set and stored, one of which is put to use by the control device after the coding of the cleaning tool being used has been detected at the beginning of the cleaning operation and, hence, the respective user has been established. To this effect the coding detection device issues a corresponding signal to the control device. Where electric toothbrushes are used, it is possible, for example, for the motor speed to be reduced from the usual speed for adults when a child is the user, so that a gentler tooth cleaning operation is performed for the child. In addition, the control device may vary, responsive to a signal from the coding detection device, the duration of a timer according to the user identified, setting the timer to two minutes for children and to three minutes for adults, for example. The type of timer signal could also be modified, as by selecting a tune for children and a buzzer tone for adults.

In a further aspect of the invention it is also possible to store, process and indicate as on a display user-specific data such as cleaning frequency, cleaning speed, cleaning time, time interval between cleaning operations or application pressure automatically in response to a corresponding signal from the detection device. This too results in enhanced user comfort.

The handle section hence detects, i.e., identifies, the individual user indirectly by referring to the cleaning tool used or its coding because each user is assigned to one or more cleaning tools of his or her own. For this purpose the cleaning tools, which otherwise may be of identical construction, may have user-specific coding elements.

Provision may also be made for a specific function control in dependence upon the particular type of cleaning tool used. For instance, operating parameters of the handle section may be varied automatically when a brush attachment with specific properties such as high or low hardness is used. Equally, another operating program may be run when a cleaning tool of different type as, for example, an interproximal cleaning tool, a tool for gum massage or a tongue cleaner is attached to the handle section. Rotational speed, desired cleaning time, driving motion, cleaning frequency, cleaning speed, application pressure threshold value, etc. can be suitably adapted in response to the individual cleaning tool and/or user.

Still further, by identifying an individual cleaning tool it is possible to establish its state of wear, for example, by determining and evaluating the time of past uses or cleaning operations of this particular cleaning tool. Where cleaning tools with chemical additives are used, their "use by" date can be identified by the date of manufacture hidden in the coding. Predetermined cleaning or maintenance intervals can also be indicated.

A variety of approaches are possible for the detection of the coding provided directly on the cleaning tools as well as the coding of the cleaning tools.

In particularly simple manner the cleaning tool is coded by its shape. It may possess one or several shaped bodies which are connected to the body of the cleaning tool fixedly or formed integrally therewith and lie in the range of detection of the coding detection device of the handle section when the cleaning tool is coupled to the handle section. The coding may embody a specific geometrical outer contour and/or a specific spatial arrangement of the shaped body relative to the coupling section of the cleaning tool and ultimately to the coding detection device on the handle section. Detection of the shaped body or bodies may be performed in noncontacting fashion using, for example, light barriers or the like.

In an embodiment of the invention the coding device of each cleaning tool is brought into mechanical contact with the coding detection device, enabling it to read the coding. This results in a particularly straightforward construction.

The handle section may include a scanning device for scanning the coding provided on the respective cleaning tool being used.

Preferably the handle section may include a movable or deformable sensing element that is moved or deformed by the mechanical coding of the cleaning tool as the latter is being seated onto the handle section. Depending on the coding, the sensing element is moved or deformed by a predetermined amount or in a predetermined direction. The sensing element produces a signal responsive to the movement or deformation so that the coding can be detected. The sensing element may also be configured in such manner that it senses a force that the coding exerts as the cleaning tool is being, seated onto the handle section. This can be accomplished, for example, by a piezoelectric design of the sensing element in which the sensing element is active itself to deliver a signal. To obtain a particularly simple configuration the sensing element may be constructed as a preferably electromechanical contact member. This member, upon being correspondingly deformed or moved by the coding of the cleaning tool, then opens or preferably closes one or several contacts so that a corresponding signal is produced.

The sensing element may be configured in such a manner that it is deformed to different degrees or moved in different directions responsive to the coding of the attached cleaning tool, correspondingly closing different contacts or a different number of contacts.

In a further aspect of the invention provision is made for several sensing elements so that different codifications of the cleaning tools cause different sensing elements or a different number of sensing elements to be actuated.

The sensing element or sensing elements may be arranged so as to be freely accessible. In this arrangement the sensing element may be brought into operative association directly with a corresponding coding element of the cleaning tool. In an advantageous embodiment of the invention the sensing element is indirectly actuatable. The sensing element may be disposed in the interior of a housing of the handle section which may have a deformable portion, for example in the form of a soft plastic portion, through which the sensing element can be actuated. This enables a sealed, fluid-tight construction of the handle section.

In another advantageous embodiment of the invention the coding detection device may include a movable probe element which is moved by the coding of the cleaning tool during its seating engagement with the handle section. The coding detection device includes a motion sensor that detects the movement of the probe element advantageously in terms of amount and/or magnitude. The different coding of different cleaning tools is preferably designed so as to effect movements of the probe element of different magnitude and/or in different directions as the cleaning tool is being attached to the handle section. Provision may be made for several probe elements so that individual probe elements or different combinations of probe elements can be actuated by differently arranged coding sections of the cleaning tools.

Various configurations are possible for the motion sensor. It may operate optically, for example, in the manner of a light barrier. It may also detect the force exerted on the probe element by a respective coding. Preferably a sensing element of the type described in the foregoing may find application, which in this case is actuated indirectly, that is, through the probe element.

A particularly advantageous embodiment of the invention resides in that the probe element is the drive shaft of the drive mechanism arranged in the handle section for driving the cleaning tool. The drive shaft may be mounted in longitudinally displaceable fashion so that it is pushed into the interior of the handle section by the coding of the cleaning tool as it is being seated onto the handle section. The use of the drive shaft as probe element obviates the need for any specific additional arrangements with regard to the sealing of the handle section.

As coding the cleaning tool preferably has an actuating surface, in particular a pressure application surface, which is constructed and arranged such as to make engagement with an engagement surface of the coding detection device when the cleaning tool is seated onto the handle section, exerting a defined effect on said surface. The actuating surface and the engagement surface thus form interacting surfaces. Provision may be made for actuating surfaces of different coding to exert different effects on the same engagement surface, moving it, for example, a greater or lesser amount. Provision may further be made for different actuating surfaces to act on different engagement surfaces, thereby enabling the coding to be read. The engagement surface on the handle section may be disposed directly on the sensing element previously described or, alternatively, on the probe element likewise described in the foregoing or like reacting member, in particular on the drive shaft of the handle section. In the last mentioned instance the actuating surface is preferably provided on a drive shaft section of the drive shaft provided in the cleaning tool. This arrangement is particularly advantageous because it makes use of the already existing coupling sections provided for the coupling of cleaning tool and handle section to detect the respective cleaning tool, thus obviating the need to provide and process additional mechanical coupling sections. The coupling section on the cleaning tool is coded by means and in the form of an actuating surface or coded differently to exert a defined effect, particularly a defined actuating motion, on the coupling section of the handle section, which for this purpose is provided with a corresponding engagement surface.

In another advantageous embodiment of the invention the coding detection device is of the noncontacting type. This has the advantage of avoiding malfunctions due to contaminated contact surfaces or wear resulting from frequent attachment and disengagement operations.

According to a further aspect of the invention the handle section may include a signal receiver or reacting member for receiving a coded signal from the cleaning tool. The handle section may also possess a signal transmitter or acting member emitting an interrogation or activation signal to the cleaning tool that responds by sending the coded signal back. The emission of the coded signal by the cleaning tool may take place actively by a corresponding signal transmitter. The possibility also exists for passive reflection to take place on the cleaning tool, which produces a corresponding coding of the signal.

The coding of the cleaning tools and the corresponding detection of such coding may be implemented in a further variety of ways. According to a preferred embodiment of the invention provision is made for a magnetic sensor that detects a magnetic coding of the respective cleaning tool attached to the handle section. The magnetic coding of the cleaning tool may take place by introducing an individually different number of magnetic particles as acting member into a portion of the cleaning tool. The magnetic sensor may be of different configurations. According to a preferred embodiment of the invention the handle section includes as reacting member a Hall sensor that provides an electrical signal corresponding to the magnetic coding of the respective cleaning tool. According to a further preferred embodiment of the invention the handle section may include an LC oscillator that is detuned by the magnetic coding of the attached cleaning tool, thus supplying different frequencies assignable to the individual users.

Another advantageous embodiment of the invention resides in the provision of reed contacts on the handle section that are actuated individually when the cleaning tools are attached to the handle section. Depending on the combination of contacts actuated, a specific user can be identified. In accordance with an advantageous embodiment of the invention provision may be made for an optical sensor for detecting an optical coding of the respective cleaning tool attached to the handle section. As optical coding a color code may be provided on the cleaning tool that is identified by a color sensor.

Advantageously the handle section may also be equipped with one or several optical waveguides exiting from the handle section and emitting an optical signal. The light signal delivered to the cleaning tool is coded by the tool and returned to the handle section which receives this coded signal by means of a corresponding sensor or detector and converts it, receiving it by means of corresponding optical waveguides and transmitting it to a corresponding sensor. The coding may take place by defined interruption or partial obstruction of the optical waveguides exiting from the handle section. Moreover, the light exiting from the handle section through the optical waveguide can be reflected differently by the toothbrush. A specific user can be identified depending on the intensity of the reflection.

According to another preferred embodiment of the invention provision may be made for a capacitive sensor for detecting a capacitive coding of the respective cleaning tool attached. In particular the handle section may have two or more capacitor plates whose capacitance is varied by the introduction of a dielectric provided on the cleaning tool. The coding of the cleaning tools may be performed by different dielectric portions on the respective cleaning tool. A specific user is then identifiable in accordance with the variation in capacitance.

In a further advantageous embodiment of the detection device provision is made for a preferably electrically operating sensor for detecting an electrical coding of the respective cleaning tool attached. The cleaning tool sends a coded electrical signal to the handle section, meaning to a signal receiver provided thereon, thus enabling the respective user or the respective cleaning tool to be identified. It is also possible for the handle section to send initially an interrogation signal to the cleaning tool, which signal is coded by the cleaning tool and subsequently sent back.

In a further aspect of the invention provision may be made for a radio device for detecting the respective cleaning tool attached by means of electromagnetic waves. In particular a transponder may be associated with the cleaning tool. The handle section initially emits electromagnetic waves for energy supply to the transponder. The transponder stores the energy and sends an individual identification back to a detector in the handle section which detects it and correspondingly identifies the respective user or cleaning tool. The characteristic features of the cleaning tool thus include the provision of a magnetic, electrical, capacitive, electromagnetic and/or mechanical coding device. Another characteristic feature may include the provision of a signal receiver for receiving a signal from the dental cleaning device and a signal transmitter for transmitting a coded signal to the dental cleaning device, with a coding device being inserted between the signal receiver and the signal transmitter for coding the received signal.

The coding device is preferably constructed as an integral part of the cleaning tool. However, it can also be designed as a separate component suitable for detachment from the remaining part of the cleaning tool or for replacement. This affords the advantage of requiring only a single mold for the manufacture of the cleaning tool. By mounting the separate coding device the cleaning tools are coded on an individual basis and assignable to a particular user.

The coding device is arranged preferably in the area of the connection between the cleaning tool and the handle section. This facilitates the reading of the coding by the recognition device on the handle section. In particular the coding device may be integrated in a ring arranged at the end of the cleaning tool close to the handle section, being in particular snap-fittable thereto by positive engagement therewith. The various configurations of the recognition devices may be provided singularly or in combination. The same applies to the various configurations of the coding device on the cleaning tool.

In summary, the present invention relates to an electromotive toothbrush comprised of a handle section and one or more user-specific attachments as, for example, brush attachments or the like, with the handle section and the brush attachment fitted to the handle section communicating with each other. The brush sections or cleaning tools may be of various designs including, for example, a child's toothbrush with soft bristles, an adult's toothbrush with hard bristles, an interproximal brush or the like, with each of these cleaning tools of different design for the intended application being assigned to a specific user. Hence a handle section usable by each user is provided, onto which user-specific cleaning tools of like or different design are plugged in order to care for or clean the respective user's teeth by means of the user-specific cleaning tool(s). The cleaning tools have an acting member or a coding communicating with a reacting member or a coding detection device in the handle section. Thus, by suitably designing the acting member(s) or coding device in the cleaning tool it is possible to inform the handle section, by way of communication between the coding device and the coding detection device, which user-specific cleaning tool, be it an interproximal cleaning tool, a toothbrush or some other cleaning tool, is currently plugged on the handle section. This possibility of detecting the user-specific or cleaning-tool-specific data of the particular cleaning tool attached to the handle section provides the prerequisite for the handle section to be able to operate the attached cleaning tool on a user- or cleaning-tool-specific basis. Thus it is possible to set, for example, the cleaning period, the cleaning speed or similar cleaning-specific parameters on a user- and cleaning-tool-specific basis by means of the handle section. Furthermore it is possible to detect user- or cleaning-tool-specific data in terms of the cleaning operation, which data can be stored, for example, in user- or cleaning-tool-specific memories of the handle section or can be indicated on a display.

Further objects, advantages, features and application possibilities of the present invention will become apparent from the subsequent description of several embodiments illustrated in the accompanying drawings.

DESCRIPTION OF DRAWINGS

FIG. 7 is a schematic view of an electric toothbrush having a magnetically coded brush attachment and a handle section with reed contacts to detect the coding according to a further preferred embodiment of the invention;

FIG. 7A is a schematic end view of the slip-on ring of the magnetically encoded brush attachment of the electric toothbrush of FIG. 7.

FIG. 9A is a schematic end view of the slip-on ring of the optically encoded brush attachment of the electric toothbrush of FIG. 9.

FIG. 18A is a schematic end view of the slip-on ring of the electromagnetically encoded brush attachment of the electric toothbrush of FIG. 18.

Like reference symbols in the drawings indicate like elements.

Figure 2:
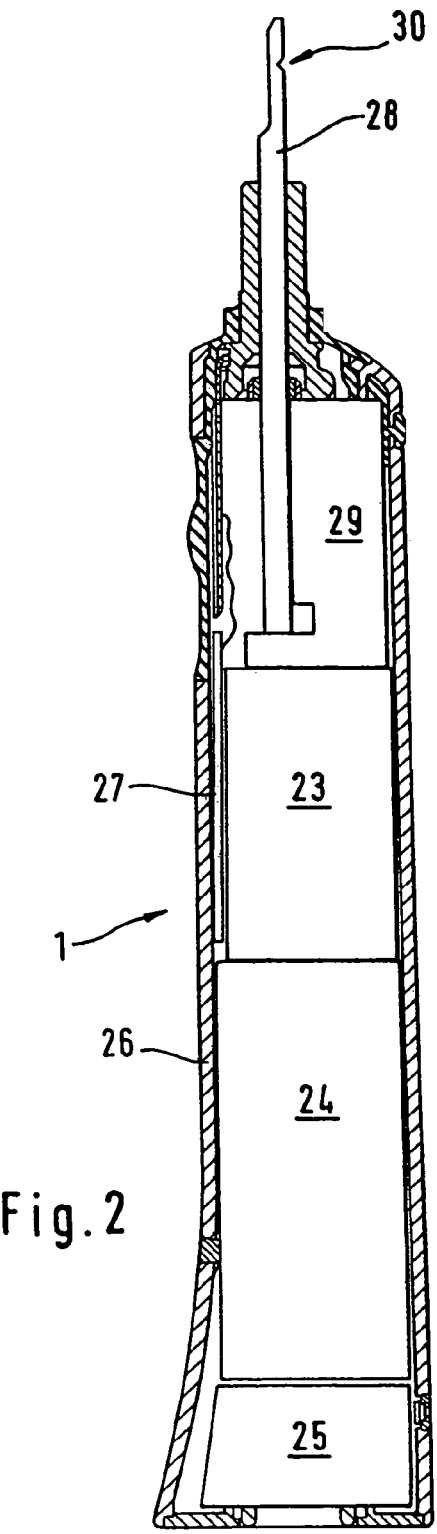
FIG. 2 is a schematic longitudinal sectional view of the handle section of the electric toothbrush of FIG. 1, showing arranged in the housing thereof the drive motor with gearing and drive shaft, the storage battery for the drive motor and the charging module for the storage battery.

The electric toothbrush shown in the Figures has a handle section 1 with a closed housing 26 accommodating, among other components and as illustrated in FIG. 2, in a manner known in the art an electric motor 23, a storage battery 24 adapted to be coupled to a charging station through a charging module 25 disposed at the bottom, and a control device 27 which may possess a printed circuit board or microprocessor. Various brush attachments 2 are seatable upon the end of the handle section 1. By means of a coupling device 3 the brush attachment 2 can be mechanically coupled to the handle section 1 in order to transmit the driving motion of the electric motor to the bristle head 4 of the brush attachment 2. The coupling device 3 comprises a positive-engagement element for positioning the cleaning tool body in its proper location and, in addition, a drive coupling which transmits the driving motion of the drive to the bristle head of the brush attachment. Protruding from the end of the handle section 1 is a drive shaft 28 adapted to be driven by the drive motor 23 via a gearing 29 in a manner equally known in the art. The drive shaft 28 has a coupling section 30 adapted to receive by positive engagement therewith a complementary coupling section of a drive shaft arranged in the cleaning tool 2, so that the driving motion is transmitted, enabling the bristle head 31 of the brush attachment to be driven in an oscillating manner.

Figure 3:
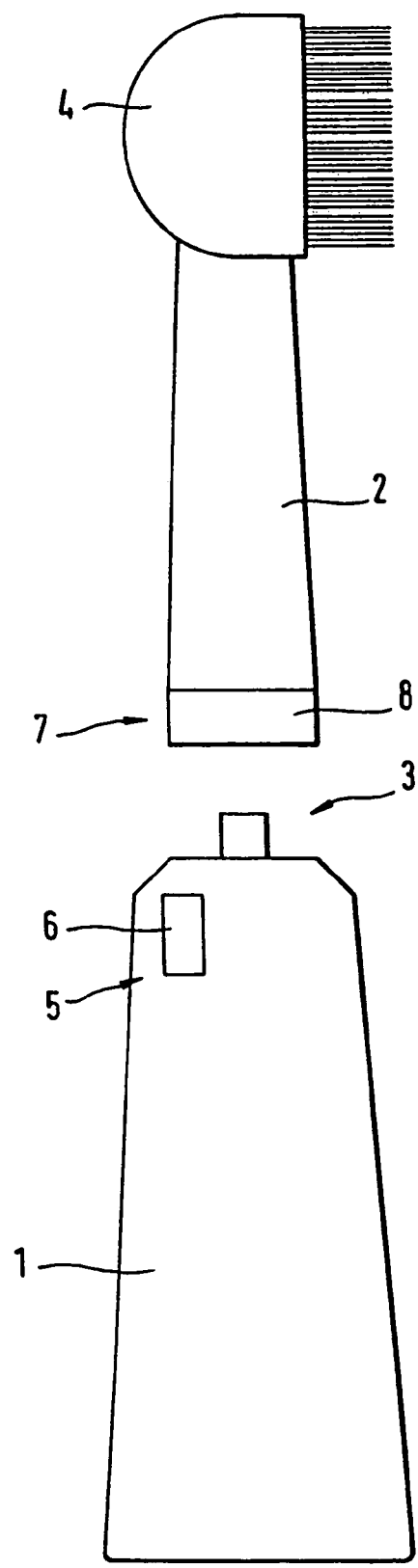
FIG. 3 is a schematic view of an electric toothbrush, showing a magnetic coding of the brush attachment and a Hall sensor for detecting the coding according to a preferred embodiment of the invention.
Figure 4:
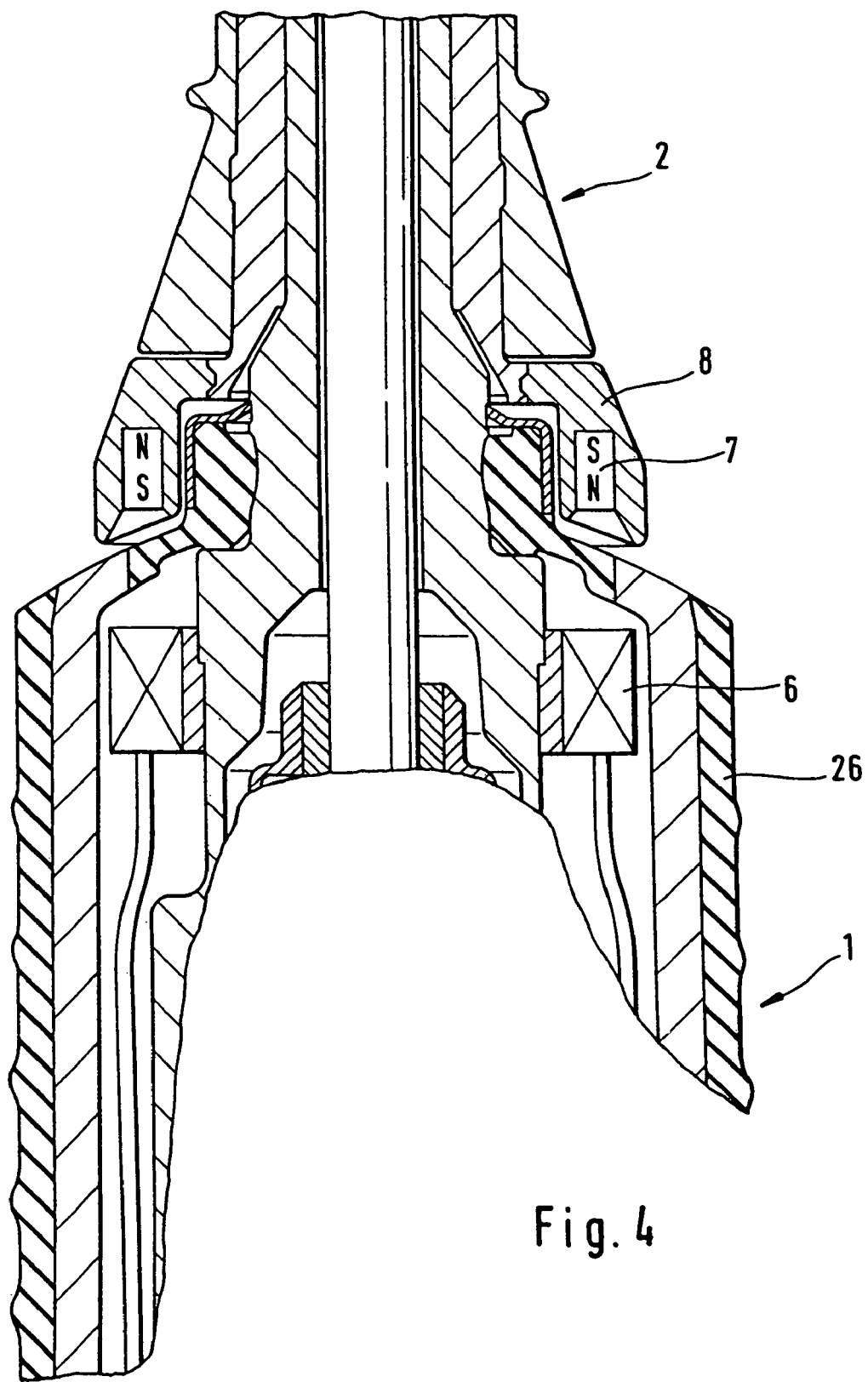
FIG. 4 is a sectional detail view of the toothbrush of FIG. 3, showing the arrangement of the Hall sensor and the magnetic coding of the brush attachment which is coupled to the handle section.

To identify the individual brush attachment 2 when attached, provision is made on the handle section for a coding detection device 5. According to FIG. 3 a Hall sensor 6 is provided at the coupling end of the handle section 1 in order to read, meaning identify, a magnetic coding 7 on the brush attachment 2. The magnetic coding 7 is formed by a slip-on ring 8 provided at the coupling end of the brush attachment 2. The slip-on ring 8 is available in a variety of colors containing, depending on the color, a different number of magnetic particles or magnetic bodies differing in number, magnetic orientation and/or magnetic field strength. As FIG. 4 shows, the slip-on ring 8 may be positioned in its proper location on the body of the brush attachment advantageously by positive engagement therewith, being in particular snap-fitted thereto. This connection may be constructed such that the ring 8 is securable to the body of the brush attachment in only one predetermined orientation relative thereto. The Hall sensor 6 in the handle section 1 supplies a signal correlating with the number of magnetic particles or the arrangement of the magnetic bodies, the value of this signal identifying the respective brush attachment 2, and hence a specific user, and being suitable for further processing by the control device in the handle section 1. The color of the slip-on-ring 8 makes it easy to remember which brush attachment 2 is assigned to which user.

As FIG. 4 shows, the magnetic coding 7 and the Hall sensor 6 are disposed at the coupling ends of the brush attachment and the handle section, respectively, lying advantageously opposite each other in order to enable an accurate detection to be accomplished.

Figure 1:
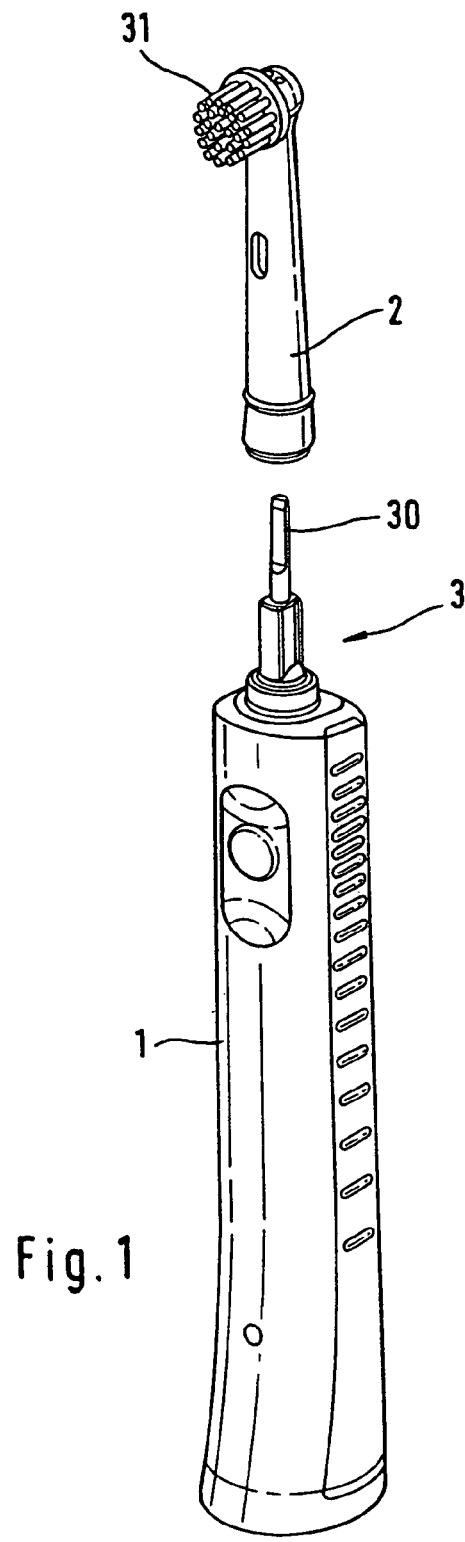
FIG. 1 is a perspective view of an electric toothbrush having a handle section and a brush attachment attachable thereto.
Figure 5:
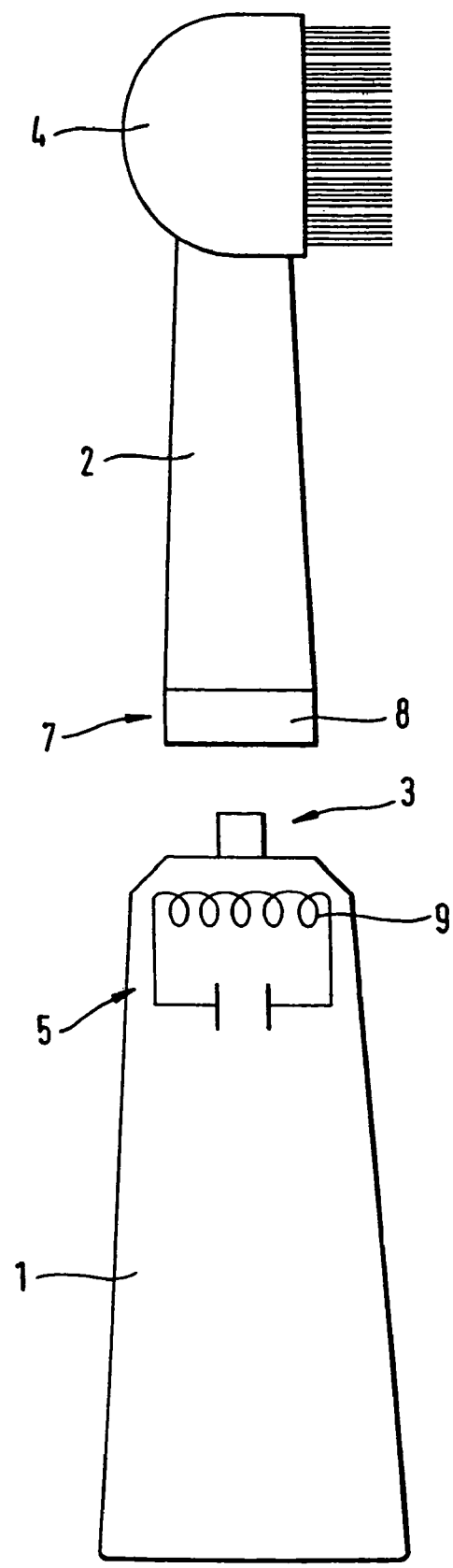
FIG. 5 is a schematic view of an electric toothbrush having a magnetically coded brush attachment and an LC oscillator in the handle section to detect the coding according to a further preferred embodiment of the invention.

The electric toothbrushes according to the further embodiments illustrated in FIG. 5 ff. are constructed basically in the same way as the toothbrush illustrated in FIGS. 1 and 2, so that like components are assigned like reference numerals, and the subsequent description deals only with the different implementations of the coding 7 of the brush attachments 2 and the corresponding coding detection devices 5 on the handle section 1. In the electric toothbrush illustrated in FIGS. 5 and 6 the brush attachment 2 carries likewise a slip-on ring 8 which is available in various colors and contains magnetic particles differing in number depending on the color. To detect the magnetic coding of the brush attachment 2, the recognition device 5 has an LC oscillator 9 which is disposed at the coupling end of the handle section 1 and detuned by the magnetic material in the brush attachment 2, thereby supplying different frequencies assignable to the brush attachments or its users. The corresponding frequency signals are further processed by the control device in the handle section 1 in order to set the corresponding operating parameters or to process and indicate the user-specific data.

Figure 6:
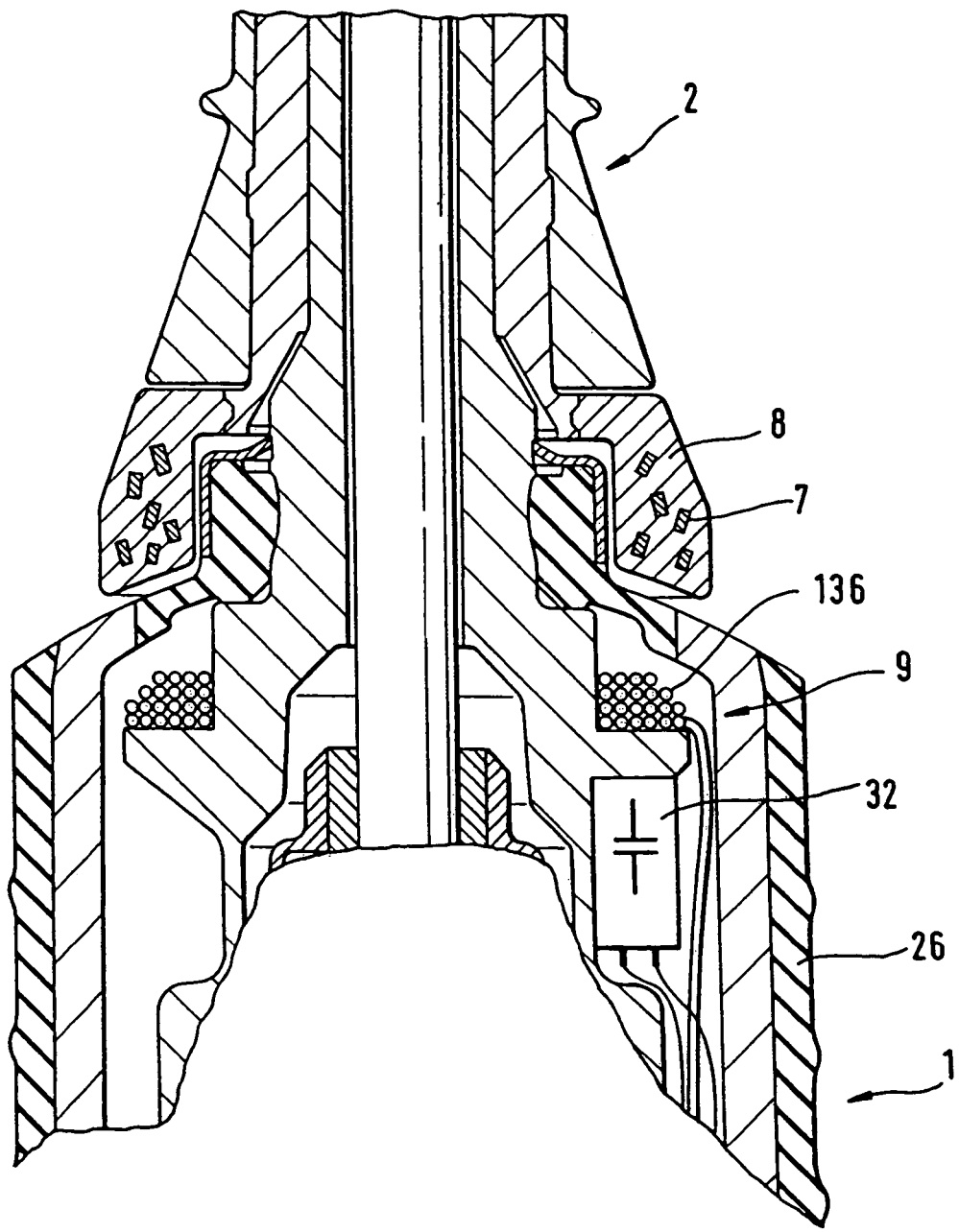
FIG. 6 is a sectional detail view of the toothbrush of FIG. 5, showing the arrangement of the LC oscillator and the magnetic coding of the brush attachment which is coupled to the handle section.

As FIG. 6 shows, the LC oscillator has a coil 136 and a capacitor 32 that are both disposed in the coupling end region of the handle section. The coil is arranged directly at the end. It may be mounted on a shoulder, or the like of a handle section chassis. The capacitor is positioned underneath the coil which faces the coding ring 8. This enables the coding to be detected with precise accuracy.

Figure 8:
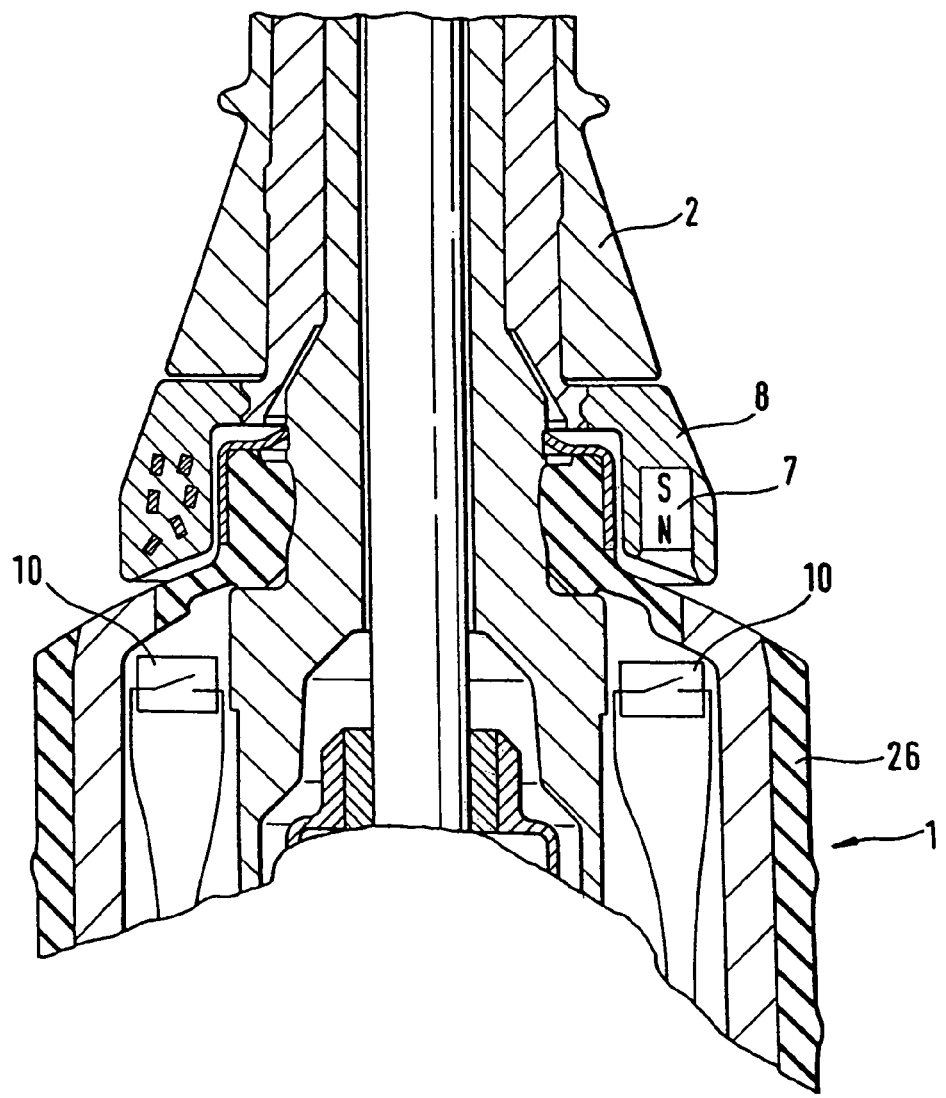
FIG. 8 is a sectional detail view of the toothbrush of FIG. 7, showing the arrangement of the reed contacts and the magnetic coding of the brush attachment which is coupled to the handle section.

FIG. 7 shows a further embodiment of an electric toothbrush in which the slip-on ring 8 of the brush attachment 2 is provided with magnetic material only at defined locations on its circumference (cf. FIG. 7a). The recognition device 5 comprises reed contacts 10 (cf. FIG. 8) arranged in the handle section 1 at the handle end close to the coupling device 3. When the brush attachment 2 is seated down onto the handle section 1, defined actuation of the reed contacts 10 takes place in accordance with the magnetic coding of the slip-on ring 8. Depending on the combination of contacts actuated, a specific user can be identified. Here too, the slip-on ring 8 is a colored ring to make it easier for the user to identify his or her assigned brush.

For enhanced response of the reed contacts, the magnetic ring 8 and the reed contacts 10 have their respective ends in relative opposite arrangement.

Figure 9:
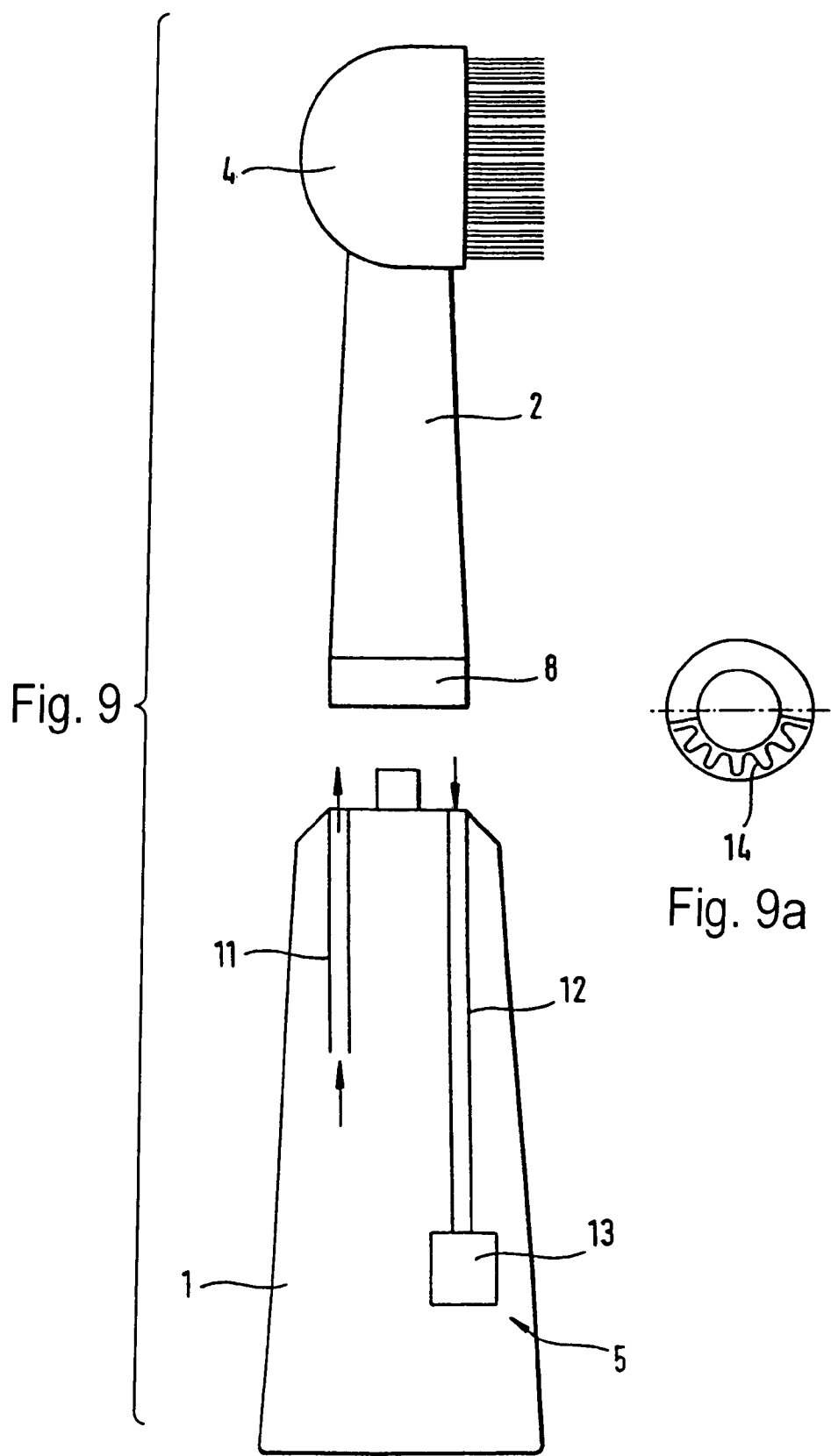
FIG. 9 is a schematic view of an electric toothbrush having an optically coded brush attachment and a handle section with optical waveguides according to a further preferred embodiment of the invention.

FIG. 9 illustrates an embodiment of an electric toothbrush in which the brush attachment 2 is detected optically. The recognition device 5 comprises in the handle section 1 one or several optical waveguides 11 exiting at the coupling end of the handle section and experiencing defined interruptions or partial obstructions by the brush attachment 2. The brush attachment 2 returns the light signal emitted from the optical waveguides 11 to the handle section 1 in coded form, the coded light signal being directed through optical waveguides 12 to a sensor 13 which detects whether and in which intensity light was returned and issues a corresponding recognition signal enabling the brush attachment to be assigned to a user. For coding and returning the light signal the brush attachment 2 may possess a preferably likewise colored slip-on ring 8 in which corresponding optical waveguides 14 are provided (cf. FIG. 9a). According to a further variant the light emitted from the handle section 1 through the optical waveguide 11 is reflected individually by the brush attachment 2 or a correspondingly coded slip-on ring 8. Depending on the intensity of reflection a particular user can be identified.

Figure 10:
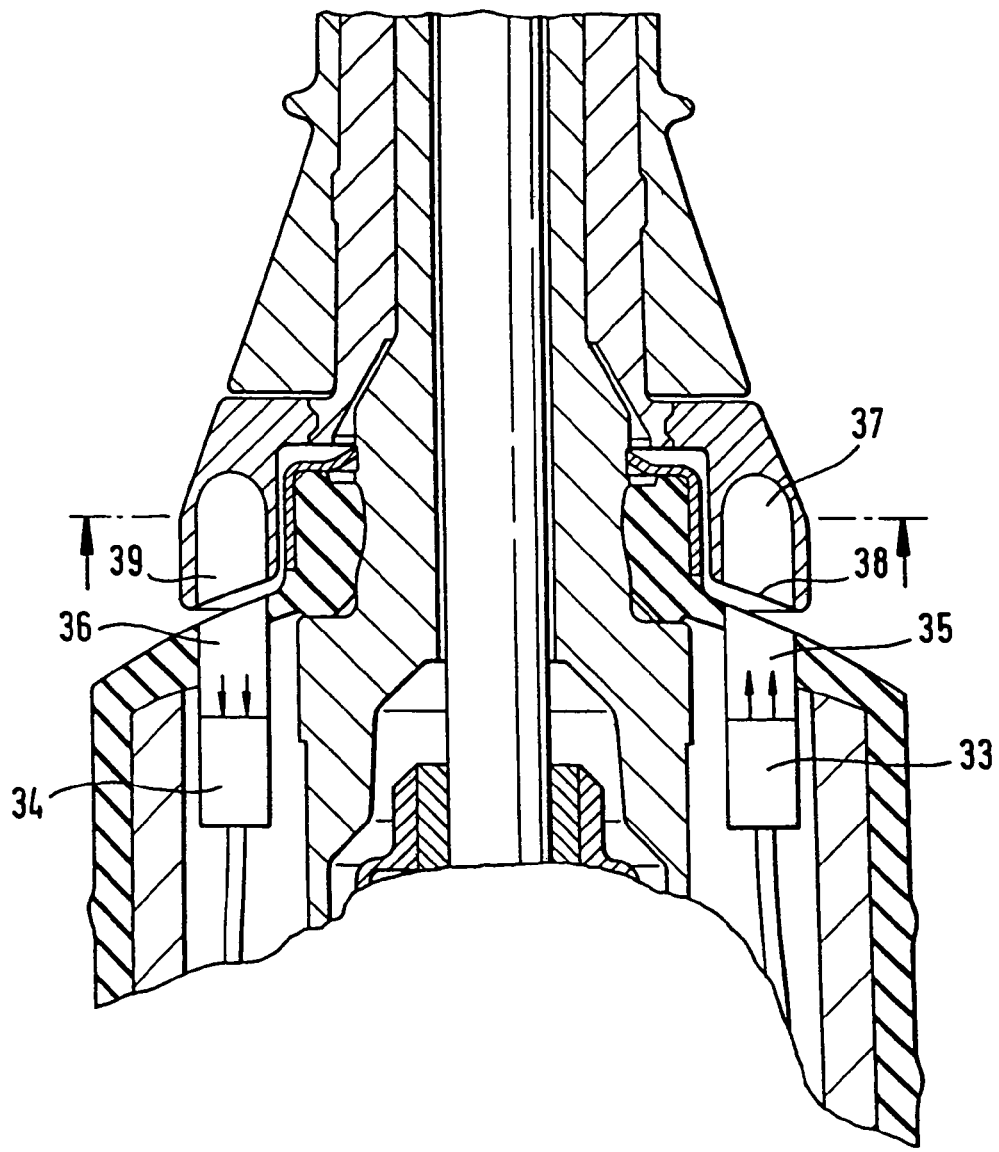
FIG. 10 is a sectional detail view of a toothbrush similar to FIG. 9, showing the arrangement of a light emitter and a light detector in the handle section and a coding of the brush attachment in the form of an optical waveguide, with the brush attachment and the handle section being shown in coupled condition.
Figure 11:
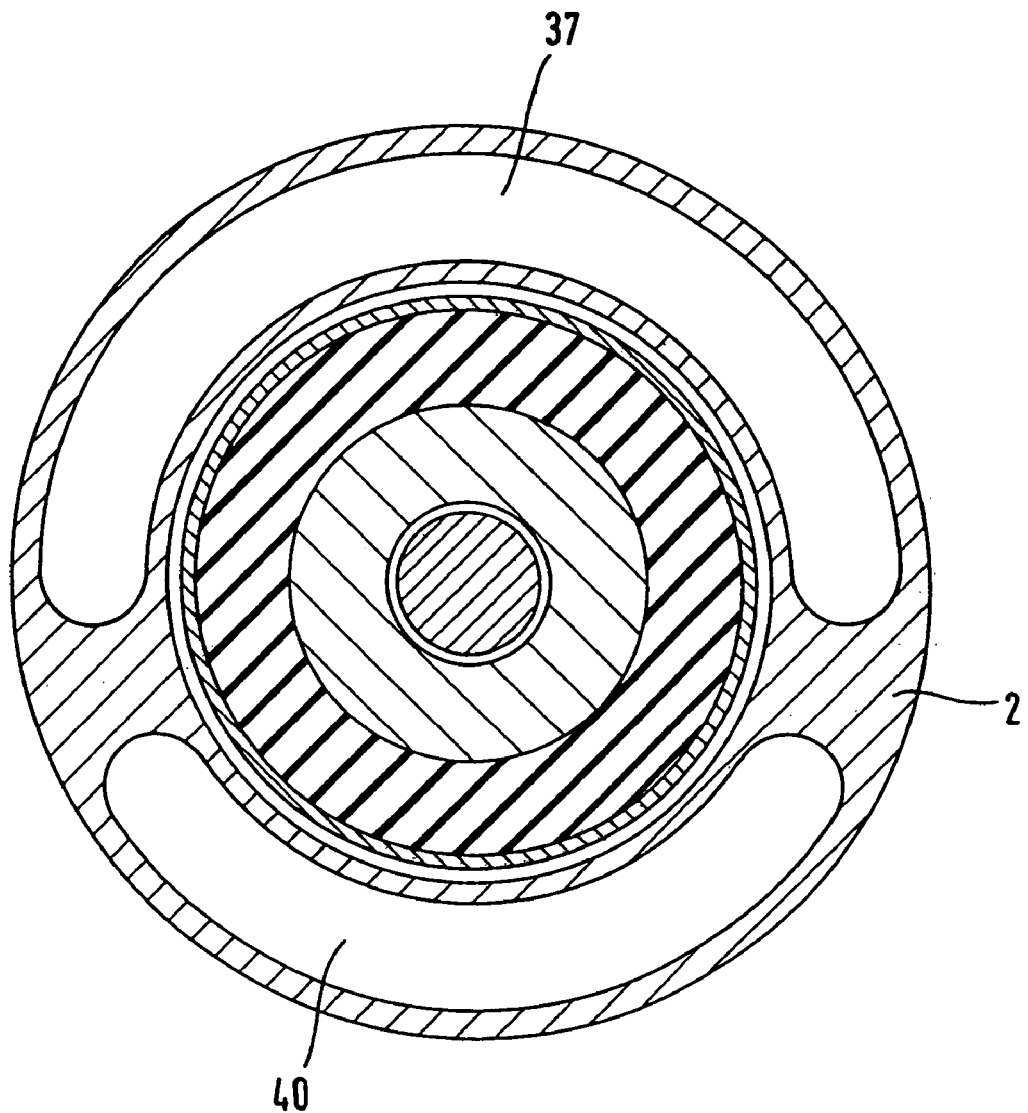
FIG. 11 is a top plan view of the optical waveguides at the end, close to the handle section, of the brush attachment of FIG. 10.

FIGS. 10 and 11 illustrate an advantageous variant of the toothbrush of FIG. 9 with optical coding of the brush attachment and corresponding detection of the coding by the handle section 1. Provided in the handle section 1 directly at its coupling end are a light emitter 33 and in circumferentially offset position a light detector 34 which, through a light exit opening 35 and a light entrance opening 36 provided at the end of the handle housing 26, look at the coupled brush attachment 2. The light exit and light entrance openings may be closed by a transparent material to obtain a closed construction of the housing 26. Both the emitter 33 and the detector 34 are connected to the control and evaluation device 27 of the handle section 1. As FIG. 11 shows, the slip-on ring 8 of the brush attachment 2 accommodates an optical waveguide 37 receiving the light emitted by the emitter 33 through a light entrance opening 38 (cf. FIG. 10), coding it and returning it through a light exit opening 39 in the slip-on ring 8 to the detector 34 in the handle section. The light may be guided in a variety of ways, particularly by reflection. In this case the optical waveguide may be configured as a reflector. The signal issued by the light detector can be evaluated by the control device of the handle section 1 to identify the respective brush attachment. The optical waveguide 37 extends in the slip-on ring 8 in an approximately arcuate configuration (cf. FIG. 11). To increase the possibilities of coding, multiple light processing devices may be provided. FIG. 11 shows a second optical waveguide 40. Coding may be performed by selection of a particular one of multiple light detectors to which the respective optical waveguide returns the received light. Coding may also be performed by the optical waveguides modifying or processing the received light in different ways, in particular reflecting it in different intensities. This is then converted into a corresponding signal by the light detector.

Figure 12:
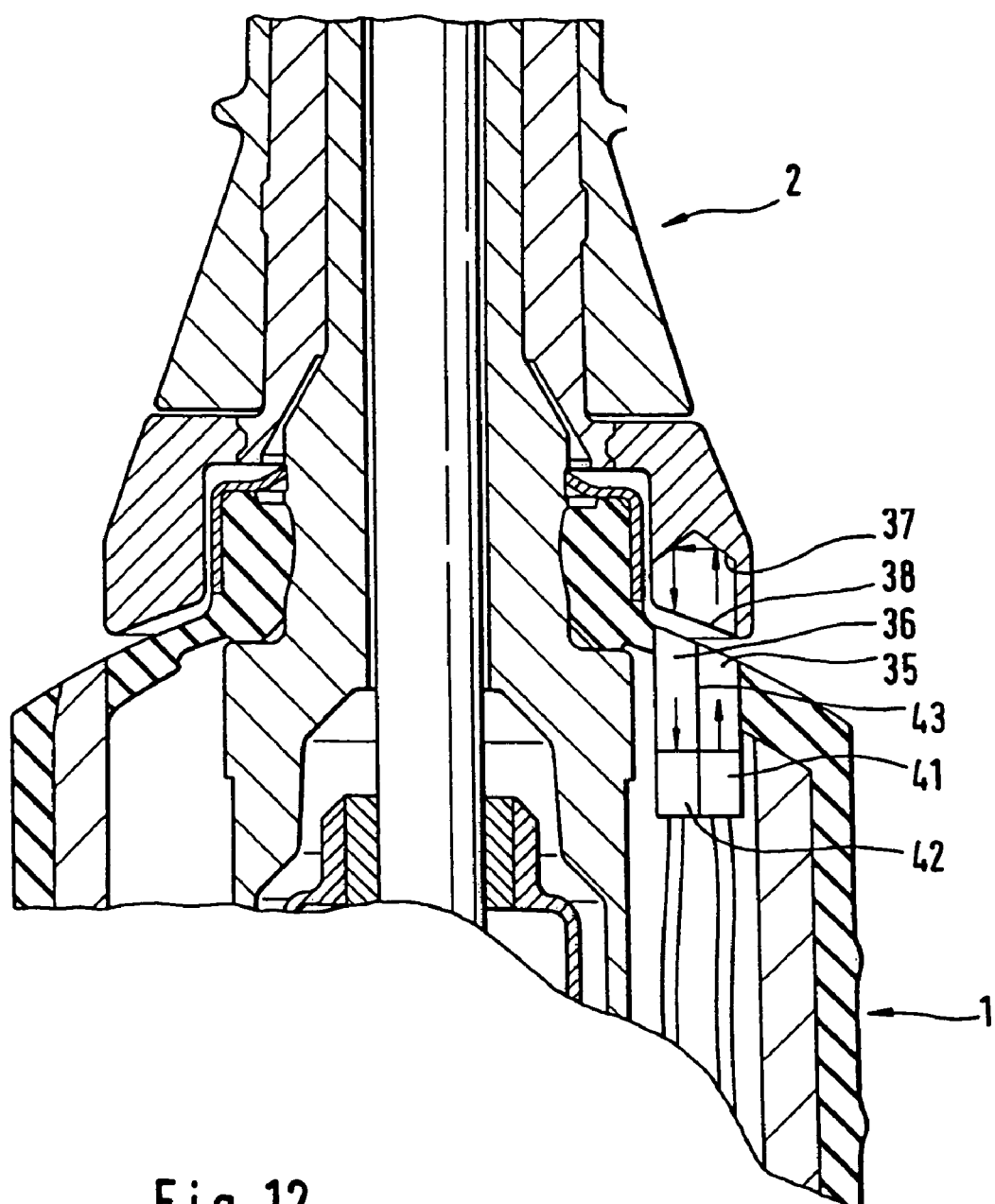
FIG. 12 is a sectional detail view of a toothbrush similar to FIG. 10, showing the arrangement of a light emitter and a light detector in the form of a single integrated component in the handle section and a coding of the brush attachment in the form of an optical waveguide, with the brush attachment and the handle section being shown in coupled condition.

FIG. 12 shows a further variant of optical coding. The light emitter 41 and the light detector 42 are constructed as an integral component. A partition wall 43 is preferably provided to separate the light entrance and light exit openings from each other. The light may be coded in particular by different magnitudes of reflection.

Figure 13:
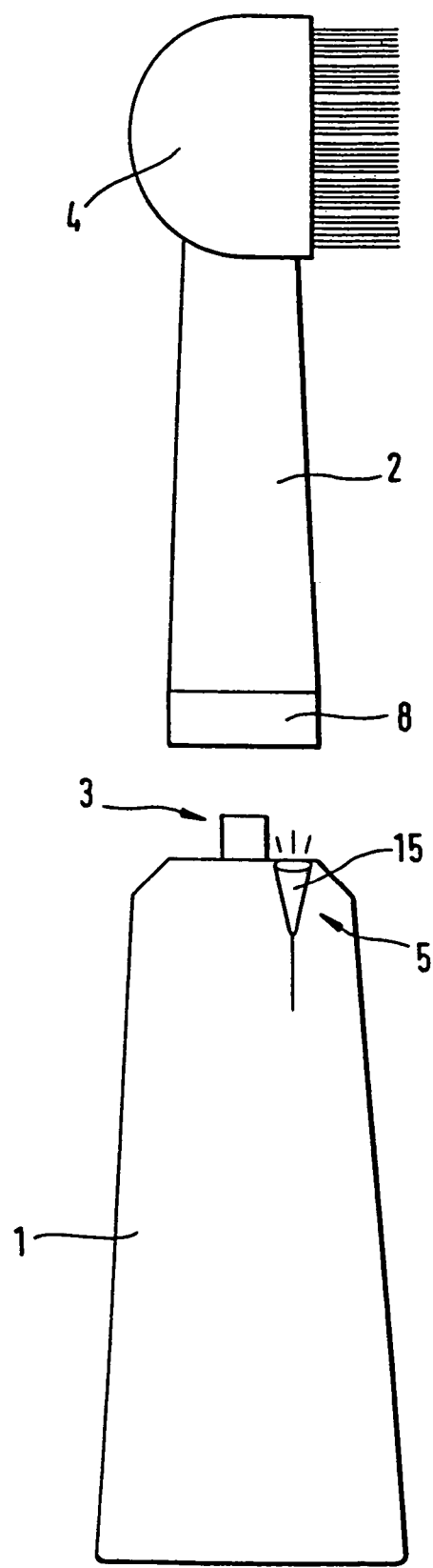
FIG. 13 is a schematic view of an electric toothbrush having an optically coded brush attachment and a handle section with color sensor for identification of the coding of the brush attachment according to a further preferred embodiment of the invention.
Figure 14:
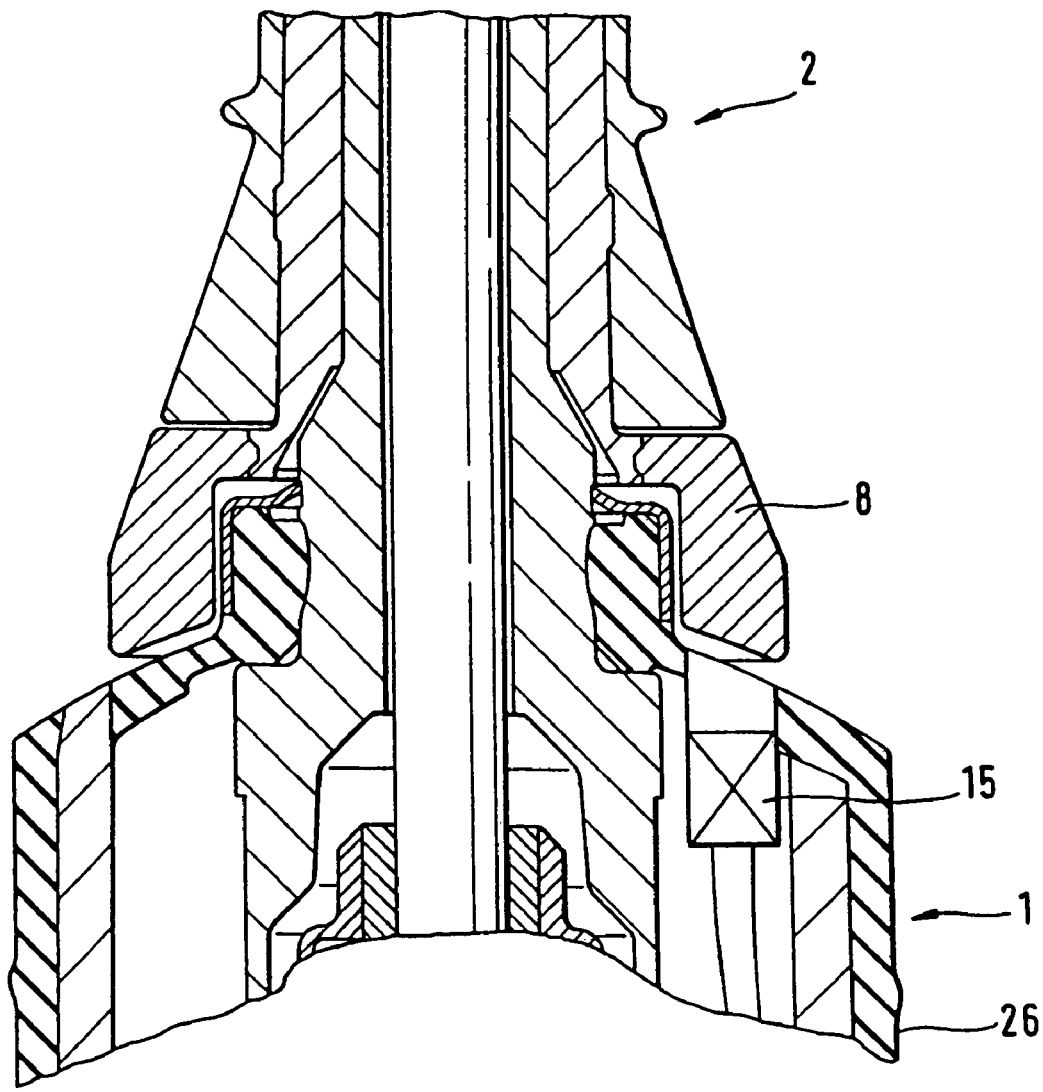
FIG. 14 is a sectional detail view of the toothbrush of FIG. 13, showing the arrangement of the color sensor in the handle section and the color code of the brush attachment which is coupled to the handle section.

The embodiment of an electric toothbrush illustrated in FIGS. 13 and 14 has similar to the preceding embodiments a colored slip-on ring 8 at the end of the brush attachment 2 close to the coupling section 30. The handle section 1 has as recognition device 5 a color sensor 15 disposed at the coupling end of the handle section 1 and oriented in the direction of the colored slip-on ring 8. The color sensor 15 detects the color of the slip-on ring 8, enabling the respective brush attachment or user of the toothbrush to be determined. Conveniently, the color sensor is arranged directly at the coupling end of the handle section 1 and oriented in the direction of the ring 8 when the brush attachment sits on the handle section 1. The color of the slip-on ring 8 preferably has fluorescent properties or other properties increasing the light intensity, thereby enabling the color of the slip-on ring 8 to be recognized by the color sensor 15 reliably.

Figure 15:
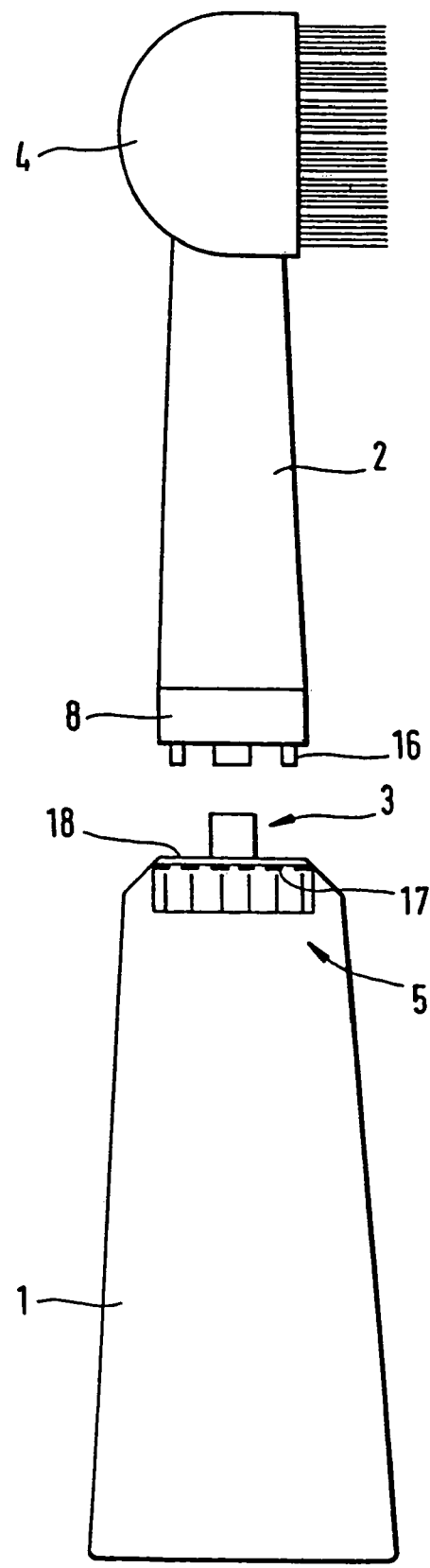
FIG. 15 is a schematic view of an electric toothbrush having a brush attachment coded mechanically by its shape in accordance with another preferred embodiment of the invention.
Figure 16:
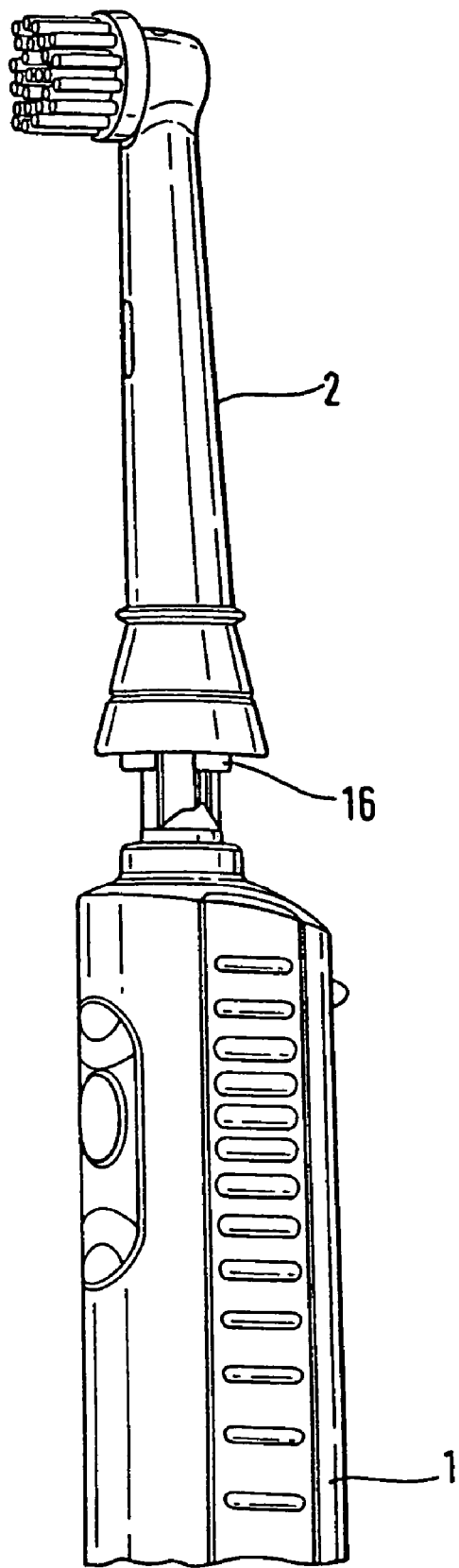
FIG. 16 is a perspective view of the toothbrush of FIG. 15, showing the brush attachment as it is being coupled to the handle section.
Figure 17:
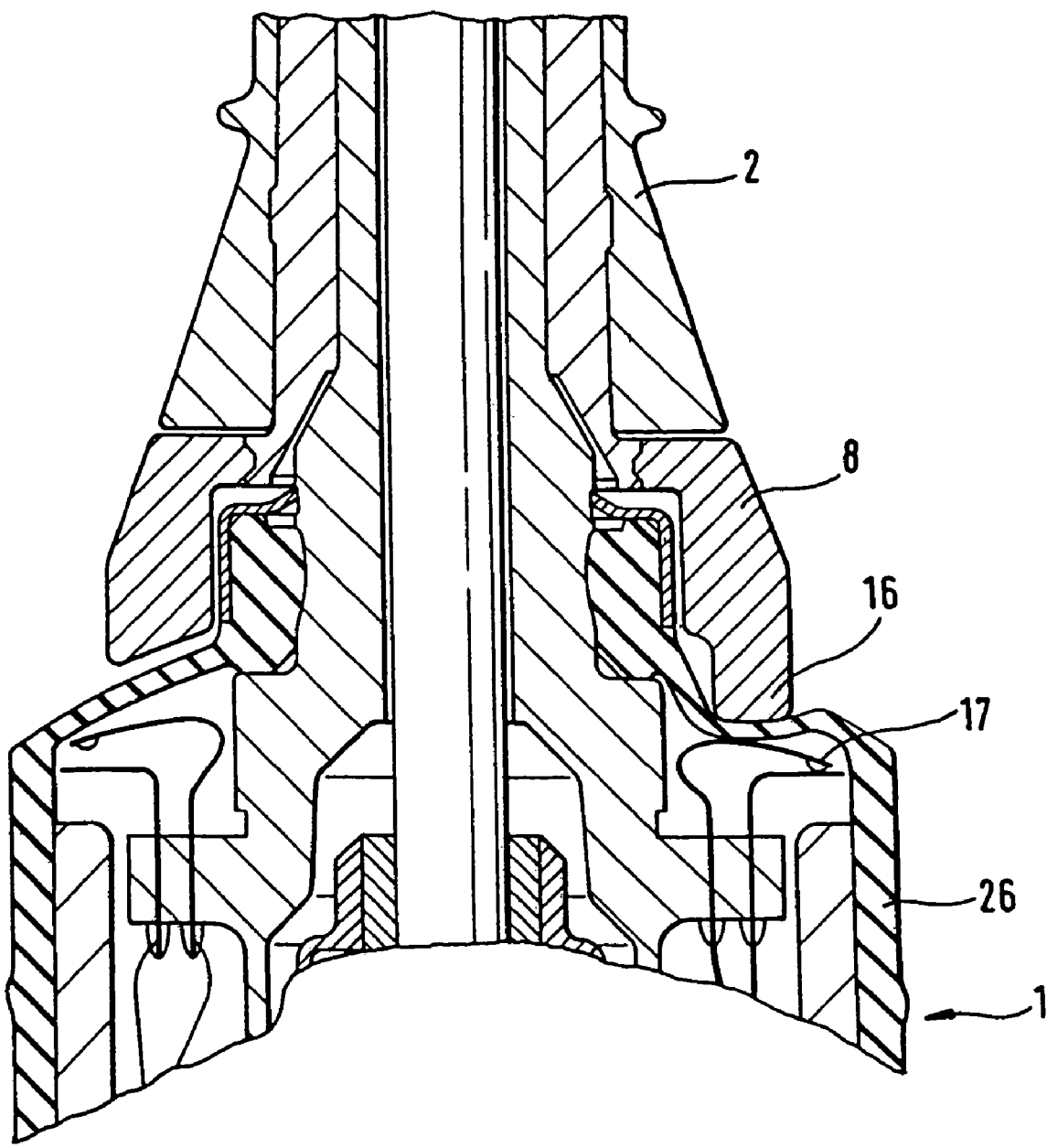
FIG. 17 is a sectional detail view of the toothbrush of FIGS. 15 and 16, showing the arrangement of the coding projections on the brush attachment and the sensing elements in the form of electromechanical contacts for sensing the coding projections, with the brush attachment and the handle section being shown in coupled condition.

FIGS. 15, 16 and 17 illustrate an embodiment of an electric toothbrush in which the brush attachments 2 are recognized mechanically. The colored slip-on ring 8 at the end of the brush attachment 2 is an individually shaped coding body having projections 16 or recesses in the form of ribs or grooves. According to one embodiment of the invention the shaped bodies extend as projections from the end of the brush attachment, in particular essentially parallel to the longitudinal axis of the brush attachment. At the opposite end of the handle section 1 provision is made for elastically deformable sensing elements in the form of mechanical contacts. 17 which are subjected to individual and defined actuation by the brush attachment 2, meaning the projections 16 on the slip-on ring 8, so that the respective brush attachment 2 is identified according to the combination of actuated contacts. The shaped coding bodies 16 have for this purpose actuating or pressure application surfaces which are arranged, oriented and/or configured such as to depress the sensing element a predetermined amount when the brush attachment is seated down on the handle section. The sensing elements generate a signal responsive to the amount of depression, in the simplest case an on-off signal according to the contacting of the contact sections provided at the sensing elements' ends. Actuation of the mechanical contacts 17 can be checked preferably electrically. To cover the mechanical contacts 17 and shield them against the environment a soft membrane 18 may be placed over the mechanical contacts 17 at the end of the handle section 1, through which membrane the mechanical contacts 17 can be actuated by the projections 16. To accomplish this the housing 26 may be a two-component injection molded part fabricated from hard and soft plastics material.

Figure 18:
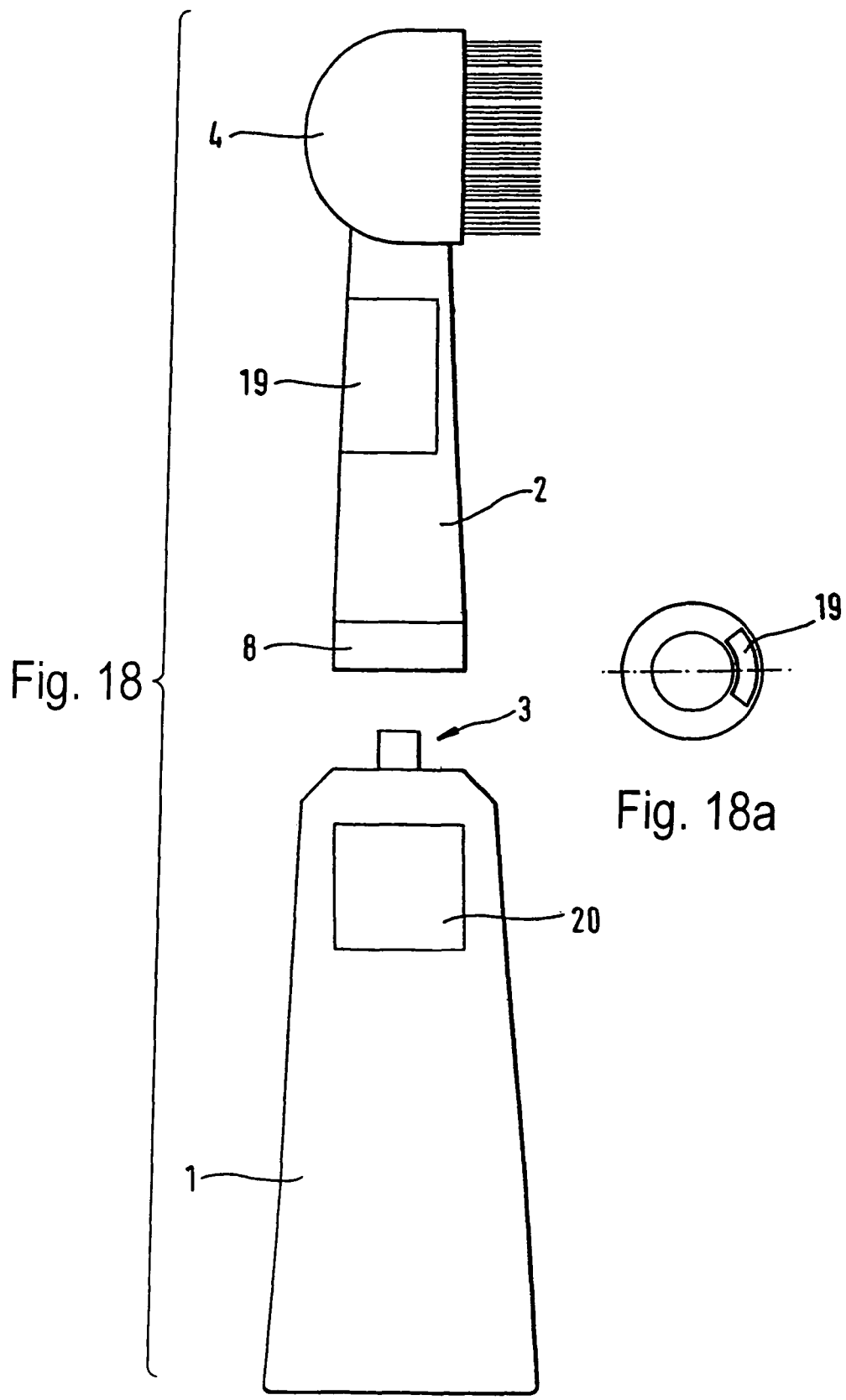
FIG. 18 is a schematic view of an electric toothbrush having an electromagnetically coded brush attachment with a transponder bonded thereto by adhesion and a corresponding detection device in the handle section according to a further preferred embodiment of the invention.
Figure 19:
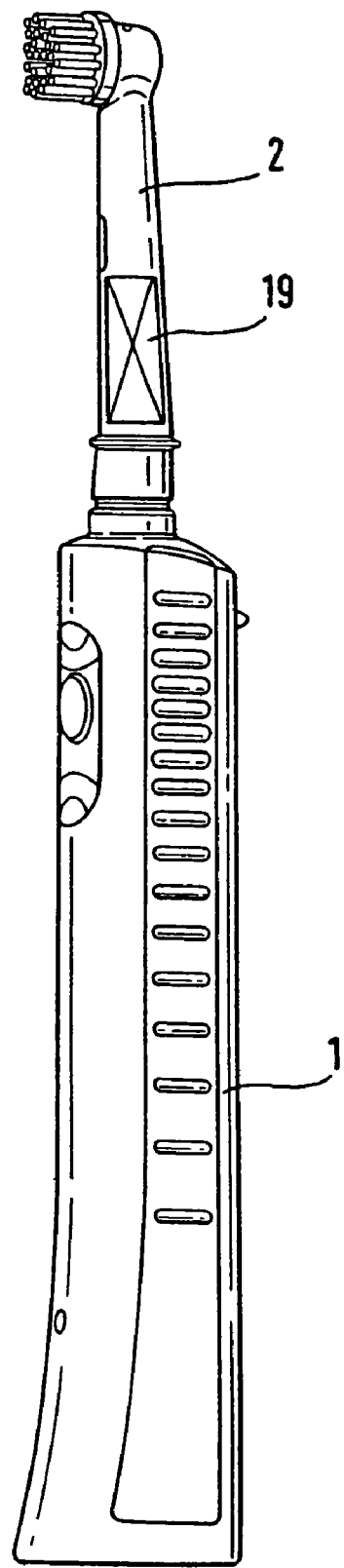
FIG. 19 is a perspective view of the toothbrush of FIG. 18.
Figure 20:
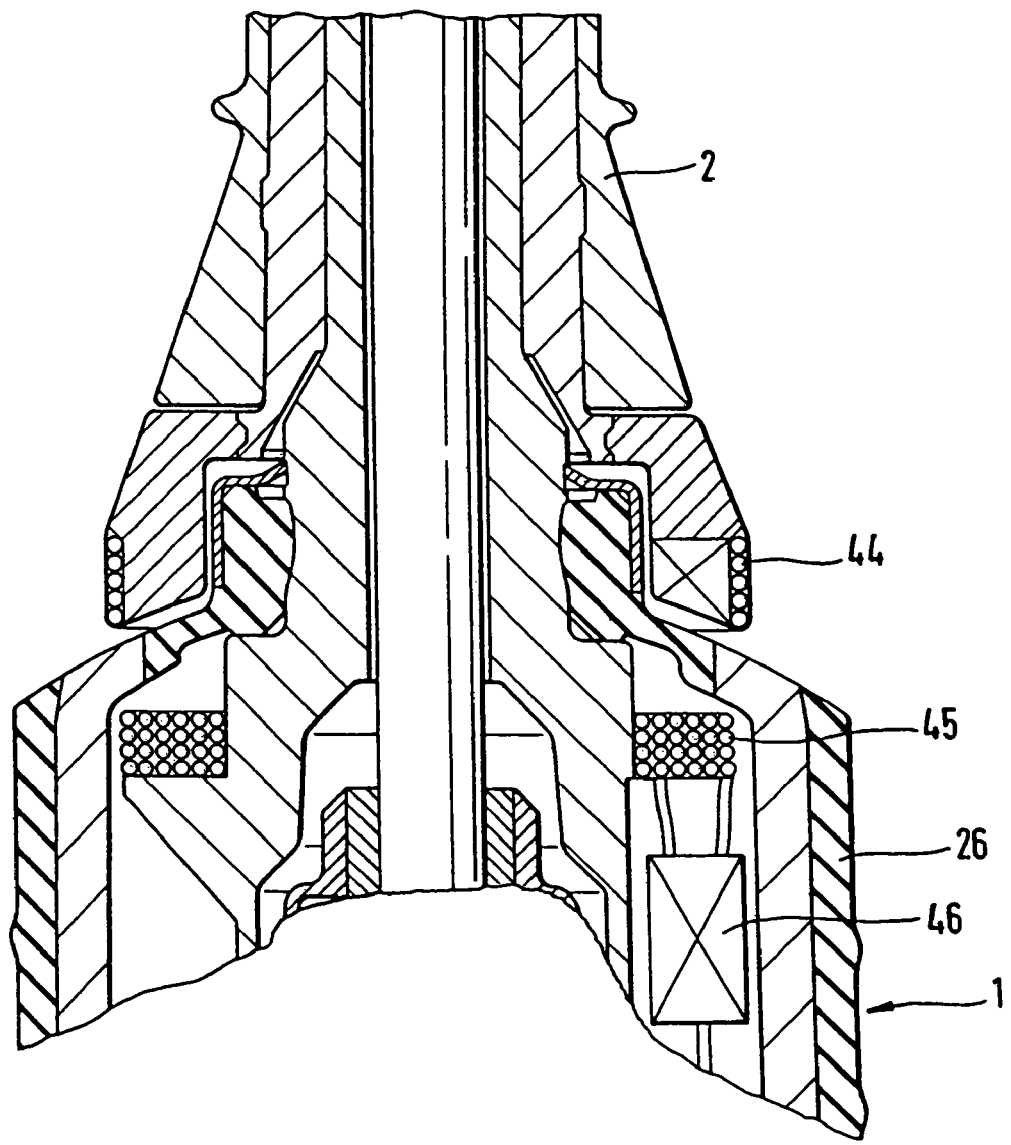
FIG. 20 is a sectional detail view of a toothbrush similar to FIGS. 18 and 19, showing the arrangement of a transponder chip in a coding ring provided at the end of the brush attachment, and a transmitter coil and a receiver coil together with an associated electronic evaluation device in the handle section, with the brush attachment and the handle section being shown in coupled condition.

FIGS. 18 to 20 illustrate a further embodiment of an electric toothbrush in which the respective brush attachment 2 is detected, i.e., identified by means of radio signals.

The brush attachment 2 is equipped with a transponder 19 which may be bonded by adhesion to the brush attachment 2 in the form of a label referred to as smart label (FIG. 19). Advantageously, the transponder 19 may also be contained in the colored slip-on ring 8 at the end of the brush attachment 2 (cf. FIGS. 18a and 20). Provided in the handle section 1 is a detector 20 tuned to the transponder 19 and serving as both a signal transmitter and a signal receiver. Via the coil 45 the detector 20 in the handle section 1 initially emits electromagnetic waves to the coil 44 connected to the transponder 19 in order to supply power to the transponder 19 or its microchip. The transponder stores the energy and sends a specific identification back to the detector 20 which receives said identification, identifies it by means of its electronic evaluation device 46 and delivers a corresponding signal to the control device 27 of the handle section 1. The coils 44 and 45 hence serve as both transmitter and receiver facility. They are disposed in relative opposite arrangement at the ends of the brush attachment 2 and the handle section 1, respectively (cf. FIG. 20). The identification sent back by the transponder 19 enables the brush attachment 2, and hence its user, to be identified.

Figure 21:
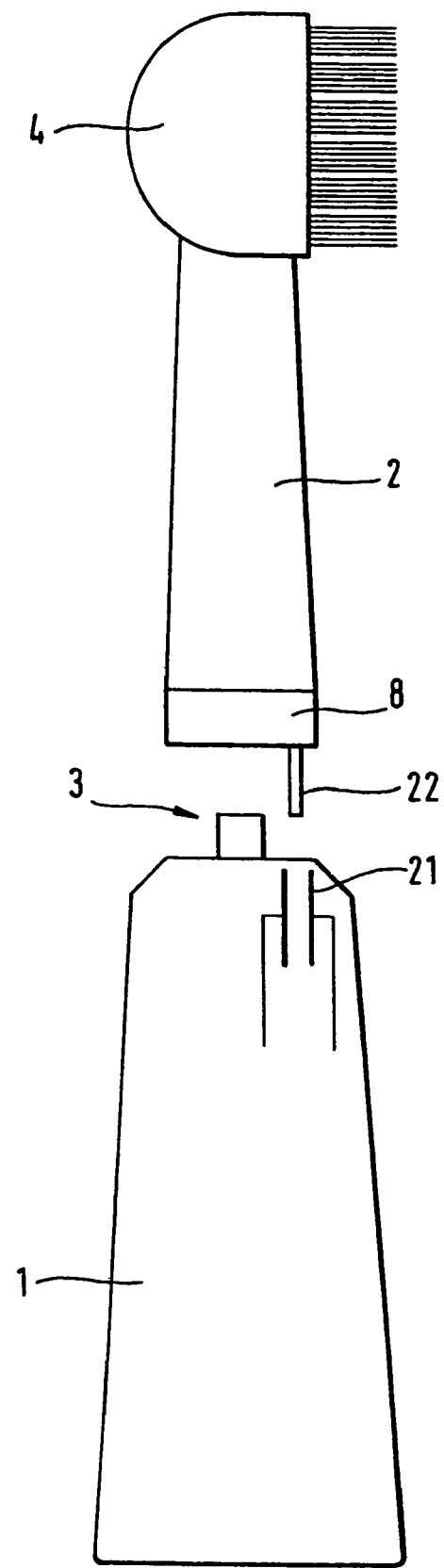
FIG. 21 is a schematic view of an electric toothbrush having a capacitively coded brush attachment and capacitor plates in the handle section to detect the coding of the brush attachment according to a further preferred embodiment of the invention.
Figure 22:
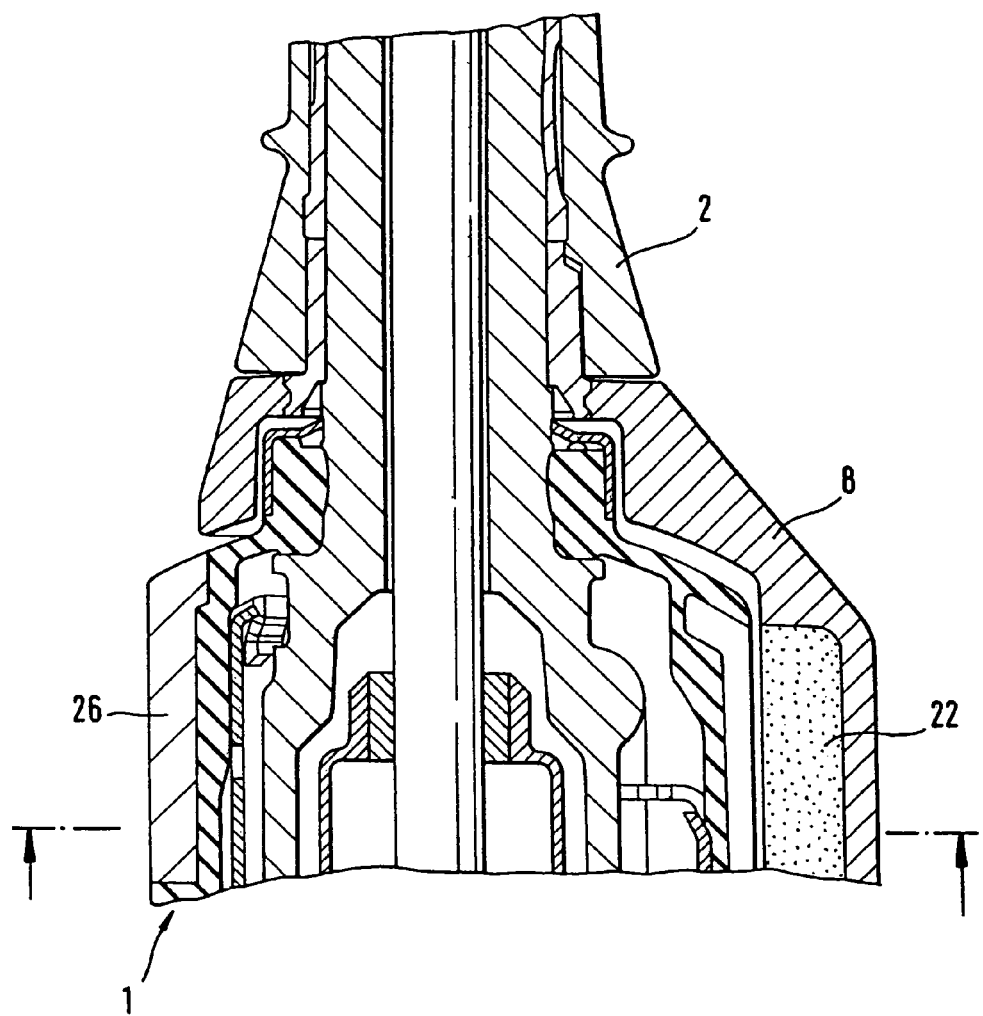
FIG. 22 is a detail view, in longitudinal section, of the toothbrush of FIG. 21, showing the arrangement of the dielectric portion of the brush attachment and the capacitor plates in the handle section, with the brush attachment and the handle section being shown in coupled condition.
Figure 23:
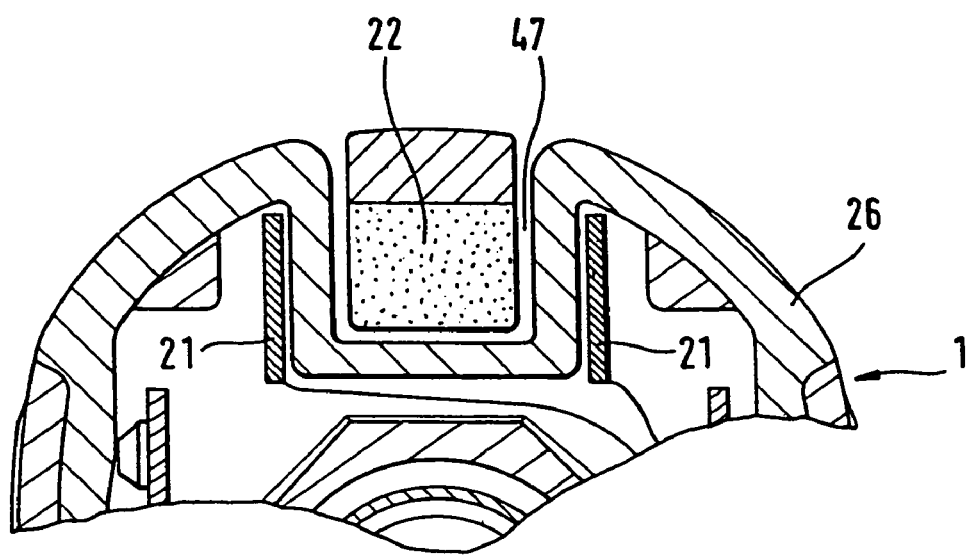
FIG. 23 is a detail view, in cross section, of the toothbrush taken along the line A-A of FIG. 22, showing the arrangement of the dielectric portion of the brush attachment and the capacitor plates in the handle section.

In the embodiment of an electric toothbrush illustrated in FIGS. 21, 22 and 23, identification of the brush attachment 2 is performed capacitively. Provided in the handle section 1 are two or more capacitor plates 21 between which a dielectric 22 is insertable to vary the capacitance of the capacitor formed by the capacitor plates 21. The dielectric 22 is arranged at the end of the brush attachment 2, and it may be in particular part of a slip-on ring 8 fittable to the brush attachment 2. The dielectric portion 22 extends preferably approximately parallel to the longitudinal axis of the brush attachment, approximately parallel to its circumferential surface. Provided in the circumferential surface of the handle housing 26 is an indentation 47 open towards the end and having the form of a longitudinally parallel groove suitable for engagement by the dielectric portion 22 of the brush attachment as it is being coupled to the handle section 1. The capacitor plates 21 are disposed in the interior of the housing 26 on either side of the indentation referred to so that the dielectric comes to lie between the capacitor plates. The use of different dielectrics makes it possible to code the brush attachments 2 individually. Depending on the capacitance or the variation in capacitance by the different dielectrics, the corresponding brush attachment 2 and hence its user can be identified. In an arrangement involving several capacitors, a coding is also obtainable by the arrangement and/or number of dielectrics.

Figure 24:
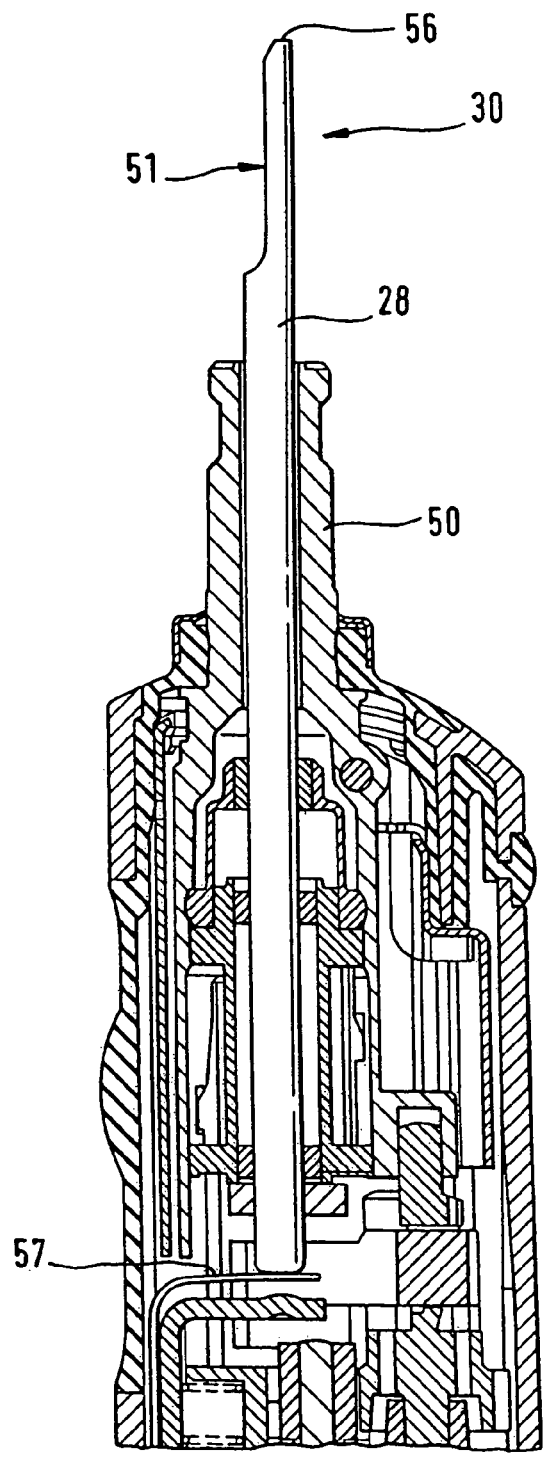
FIG. 24 is a sectional view of a handle section having a longitudinally displaceable drive shaft and an electromechanical sensing element for detecting the displacement of the drive shaft according to a further preferred embodiment of the invention.
Figure 25:
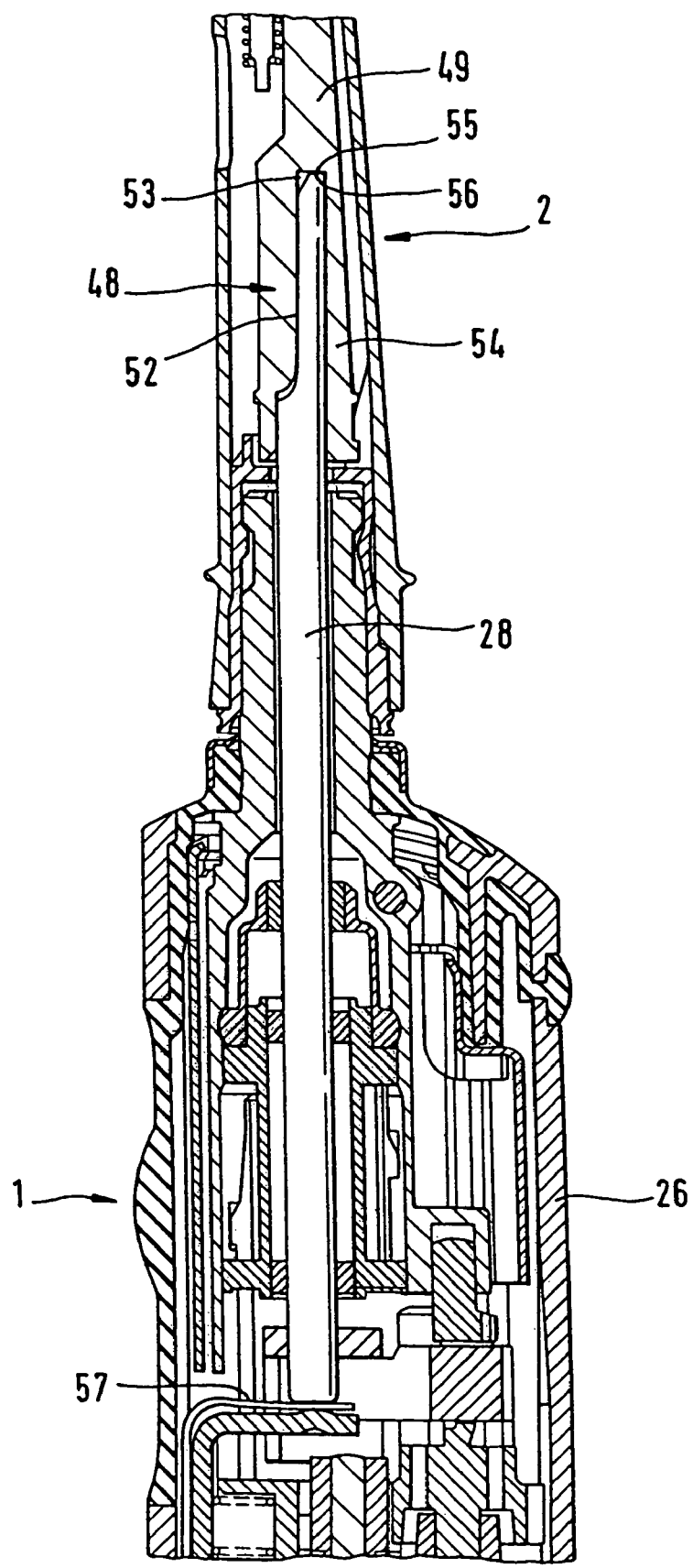
FIG. 25 is a sectional view of the handle section of FIG. 23, showing the brush attachment in coupled condition.

FIGS. 24 and 25 illustrate a specific embodiment of the invention involving a brush attachment coded mechanically, that is, by its shape, and a mechanical detection of this coding. The coding of the brush attachment is part of its coupling section 48 used for coupling the drive train 49 in the brush section with the drive shaft 28 in the handle section, to be more precise, with the coupling section 30 thereof. As FIG. 25 shows, the body of the brush attachment is seated onto a brush mount 50 of the handle section 1 with an exact fit so that the brush attachment sits firmly on the handle section 1. By means of detent noses and corresponding recesses the brush attachment is secured in place by making positive engagement with the handle section, that is, its brush mount. Axial securing can be accomplished also by frictional engagement. When the brush attachment is pushed onto its mount, the coupling sections 48 and 30 in the drive train also make interfitting engagement. The coupling sections are formed by a shaft stub and a complementary recess in the form of a blind-end hole in the opposite shaft end, thus enabling the shaft stub to be an exact fit within the blind-end type shaft bore. Torque transmission takes place preferably by positive engagement.

The coupling sections have complementary mating surfaces 51 and 52, preferably in the form of a flattening on the drive shaft 28 and a corresponding bore secant surface in the recess 53 of the drive shaft portion 54 of the brush attachment. A spline or a splined-shaft profile may also be provided for torque transmission.

The brush attachment, in particular the coupling section 48, has as coding an actuating surface 55 which in coupled condition is in engagement with an associated engagement surface on the handle section 1, in particular on the coupling section 30 of the drive shaft 28. The actuating surface 55 mates with the engagement surface 56 in such manner that a predetermined interaction occurs between these two surfaces in coupled condition. In particular the actuating surface 55 is arranged and aligned so as to exert a predetermined pressure on the engagement surface 56. To be able to read or scan the configuration of the actuating surface 55, the associated engagement surface 56 is formed on a movable probe element, producing as interaction a predetermined movement of the probe element. It will be understood that it is also possible to detect a force, but a movement can be detected with greater ease. Different configurations of the actuating surfaces 56 are translated into different movements of the associated engagement surface 56 of the probe element.

As probe element the drive shaft 28 of the handle section is advantageously used. The drive shaft is mounted longitudinally displaceably and preferably biased into protrusion from the handle section by means of biasing members. When the brush attachment 2 is seated down on the handle section the brush attachment's actuating surface 55 urges the drive shaft 28 a predetermined distance into the interior of the handle section 1. The displacement is detected by a motion sensor which may embody a variety of configurations, being operable for example as a light barrier. Other displacement sensors may also be employed. Preferably provision may be made for an elastically deformable-sensing element with electromechanical contact of the type previously described with reference to FIG. 17. The drive shaft 28 preferably sits with a lug, preferably with its end remote from the coupling section 30, on the sensing element 57. The sensing element may at the same time serve as biasing member. When the drive shaft 28 is pressed down, the sensing element produces a corresponding signal, in particular opening or closing a corresponding contact. By suitably constructing the sensor or sensing element or multiple sensing elements the coding of the brush attachment can be read.

As FIG. 25 shows, the actuating surface 55 is formed by the bottom surface of the blind-end type recess 53 in the brush attachment's drive shaft. The associated engagement surface is formed by the end of the drive shaft 28. While being reversible, this arrangement is preferably configured as illustrated.

Alternative embodiments of the actuating and engagement surfaces 55 and 56, respectively, are possible. In a further aspect of the invention provision may be made for conical mating surfaces. Other configurations may also be contemplated.

A number of embodiments of the invention have been described. Nevertheless, it will be understood that various modifications may be made without departing from the spirit and scope of the invention. For example, identification of a brush attachment may be accomplished by any number or combinations of electronics components, including capacitors, LC oscillators and other common components. Accordingly, other embodiments are within the scope of the following claims.

The invention claimed is:

1. A cleaning tool for use with a handle section, comprising a cleaning tool coupling section to effect coupling of the cleaning tool to a handle section, and comprising a coding device for providing a coded signal that enables a handle section to identify the cleaning tool, wherein the coding device is integrated in a ring arranged at a coupling end of the cleaning tool, being snap-fittable to the cleaning tool by positive engagement therewith.

2. The cleaning tool as claimed in claim 1, wherein the coding device includes a signal receiver for receiving a signal from a handle section and a signal transmitter for transmitting a coded signal to a handle section.

3. The cleaning tool as claimed in claim 2, wherein coding elements are provided between the signal receiver and the signal transmitter for coding the received signal.

4. The cleaning tool of claim 2, wherein said signal receiver is a transponder chip.

5. The cleaning tool as claimed in claim 1, wherein the coding device possesses a coding body, which is fixedly connected to the body of the cleaning tool and arranged and configured so as to be positioned in the range of detection of a coding detection device of a handle section when the cleaning tool and a handle section are coupled.

6. The cleaning tool as claimed in claim 1, comprising at least one actuating section as a mechanical coding device configured to activate on coupling of the cleaning tool to a handle section.

7. The cleaning tool as claimed in claim 6 wherein an actuating section of an actuating surface registers with a corresponding engagement surface associated with a sensing element of a handle section in such manner that on coupling of the cleaning tool to a handle section the engagement surface on a handle section is moved by a predetermined amount or in a predetermined direction or is acted upon by a predetermined force.

8. The cleaning tool as claimed in claim 1, wherein the coding device includes at least one dielectric coding body which is arranged in the area of a coupling end of the cleaning tool, being constructed to protrude beyond the end in particular in the direction of the coupling motion.

9. The cleaning tool as claimed in claim 1, wherein the coding device includes an optical waveguide communicating with a light entrance opening and a light exit opening provided in the coupling end of the body of the cleaning tool.

10. The cleaning tool as claimed in claim 1, wherein the coding device is an integral part of the cleaning tool.

11. The cleaning tool as claimed in claim 1, wherein the coding device is connected to the cleaning tool releasably.

12. The cleaning tool of claim 1, wherein the cleaning tool coding device is an electromagnetic coding device.

13. The cleaning tool of claim 1 wherein the cleaning tool coupling section is a mechanical coding device.

14. The cleaning tool as claimed in claim 13, wherein the mechanical coding device is configured in such manner as to cooperate with a drive shaft of a handle section, being a section of a drive shaft of the cleaning tool.

15. The cleaning tool as claimed in claim 13, wherein the mechanical coding device includes at least one magnetic coding body which is arranged in the area of a coupling end of the cleaning tool.

16. An oral care device, comprising:
a cleaning tool portion having a cleaning section in the vicinity of one end thereof;
a handle portion, with a driver assembly therein for driving the cleaning section, wherein the cleaning tool portion and the handle portion are adapted such that the cleaning tool portion is connectable to the handle portion;
communication means for noncontacting electromagnetic data communication between the cleaning tool portion and the handle portion when the cleaning tool portion and handle portion are joined together;
an electrical memory element in the cleaning tool portion that stores at least data that identifies the cleaning tool portion; and
an electronic control device in the handle portion, wherein the memory element in the cleaning tool portion provides data therein to the electronic control device via the communication means.

17. An oral care device of claim 16, wherein the electronic control device in operation accumulates data concerning use of the cleaning tool portion, and wherein the oral care device includes means for reading data in the memory element in the cleaning tool portion to the electronic control device.

18. An oral care device of claim 16, wherein the data is used to monitor use of the oral care device.

19. An oral care device of claim 16, wherein the oral care device will not operate unless the data from the memory element is valid, as determined by the electronic control device.

20. An oral care device of claim 16, further including a device for providing operating data to define particular operations of the cleaning tool portion.

21. An oral care device of claim 16, wherein the electronic control device includes means for evaluating the time of past uses of the cleaning tool portion.

22. An oral care device of claim 16, wherein the oral care device comprises a toothbrush and the cleaning tool portion comprises a brushhead portion.

23. An oral care device of claim 16, wherein the cleaning tool portion comprises a bristle section, an interproximal cleaning section, a gum massager section, or a tongue cleaning section.

24. An oral care device of claim 16, wherein the memory element stores data that indicates one or more operating parameters for use with the cleaning tool portion.

25. An oral care device of claim 24, wherein the operating parameters comprise cleaning frequency, cleaning speed, cleaning time, cleaning threshold value, driving motion, or range or value of application pressure of the cleaning section.

26. An oral care device of claim 24, wherein the electronic control device is configured to store a user profile defining at least one of the operating parameters.

27. An oral care device of claim 24, wherein the electronic control device uses the data from the cleaning tool portion to adapt one or more operating parameters of the oral care device.

28. An oral care device of claim 16, wherein the communication means includes electrically conductive elements.

29. A cleaning tool portion of an oral care device, the oral care device including a handle portion to which the cleaning tool portion can be coupled, the cleaning tool portion comprising:
a cleaning section in the vicinity of one end of the cleaning tool portion;
communication means for noncontacting electromagnetic data communication between the cleaning tool portion and a handle portion; and
an electrical memory element in the cleaning tool portion that stores data identifying the cleaning tool portion.

30. A cleaning tool portion of claim 29, wherein the communication means includes electrically conductive elements.

31. A cleaning tool portion of claim 29, wherein the oral care device is a toothbrush and the cleaning tool portion comprises a brushhead portion.

32. A cleaning tool portion of claim 29, wherein the cleaning tool portion comprises a bristle section, an interproximal cleaning section, a gum massager section, or a tongue cleaning section.

33. A cleaning tool portion of claim 29, wherein the memory element stores data that indicates one or more operating parameters for use with the cleaning tool portion.

34. A cleaning tool portion of claim 33, wherein the operating parameters comprise cleaning frequency, cleaning speed, cleaning time, cleaning threshold value, driving motion, or range or value of application pressure of the cleaning section.

35. An oral care device, comprising:
a cleaning tool portion having a cleaning section in the vicinity of one end thereof;
a handle portion, with a driver assembly therein for driving the cleaning section, wherein the cleaning tool portion and the handle portion are adapted such that the cleaning tool portion is connectable to the handle portion;
communication means for noncontacting electromagnetic data communication between the cleaning tool portion and the handle portion when the cleaning tool portion and handle portion are joined together;
an electrical memory element in the cleaning tool portion that stores at least data that identifies the cleaning tool portion and data that indicates one or more operating parameters for use with the cleaning tool portion; and
a microcontroller in the handle portion, wherein the memory element in the cleaning tool portion provides data therein to the microcontroller via the communication means.

36. A cleaning tool portion of an oral care device, the oral care device including a handle portion to which the cleaning tool portion can be removably joined, the cleaning tool portion comprising:
a cleaning section in the vicinity of one end of the cleaning tool portion;
communication means for electrical or electromagnetic data communication between the cleaning tool portion and the handle portion; and
an electrical memory element in the cleaning tool portion that stores data identifying the cleaning tool portion and data that indicates one or more operating parameters for use with the cleaning tool portion.

37. A handle section of an electric dental cleaning device, with a coupling section for the coupling of a cleaning tool and a drive mechanism for driving a respective coupled cleaning tool, the handle section comprising a noncontacting coding detection device for detecting an individual coding received from an electrical memory element of a respective cleaning tool attached to the handle section and a control device for the control of an electric dental cleaning device in dependence upon the detected coding, wherein the control device identifies a cleaning tool based on a detected individual coding and determines a state of wear of the identified cleaning tool, wherein the control device further provides an indication that the state of wear of the identified cleaning tool is such that the identified cleaning tool should be replaced, and wherein the handle section further comprises a display that provides the indication.

38. The handle section of claim 37, wherein the control device determines the state of wear of the identified cleaning tool by evaluating the time of past uses of the identified cleaning tool.

39. The handle section of claim 37, wherein the control device determines the state of wear of the identified cleaning tool by evaluating the time of cleaning operations of the identified cleaning tool.

* * * * *